US012774407B2

(12) United States Patent

Haddleton et al.

(10) Patent No.: US 12,774,407 B2

(45) Date of Patent: Oct. 27, 2026

(54) PATCH

(71) Applicant: MEDHERANT LTD, Warwickshire (GB)

(72) Inventors: David Haddleton, Warwickshire (GB); Gabit Nurumbetov, Warwickshire (GB); Vasiliki Nikolaou, Warwickshire (GB); Andrew Ross, Warwickshire (GB)

(73) Assignee: Medherant Ltd. (GB)

( * ) Notice: Subject to any disclaimer, the term of this patent is extended or adjusted under 35 U.S.C. 154(b) by 66 days.

(21) Appl. No.: 18/690,016

(22) PCT Filed: Sep. 6, 2022

(86) PCT No.: PCT/GB2022/052261

§ 371 (c)(1),
(2) Date: Mar. 7, 2024

(87) PCT Pub. No.: WO2023/037099

PCT Pub. Date: Mar. 16, 2023

(65) Prior Publication Data

US 2024/0425731 A1 Dec. 26, 2024

(30) Foreign Application Priority Data

Sep. 8, 2021 (GB) ..................................... 2112812

(51) Int. Cl.

*C09J 175/02* (2006.01)
*A61K 9/70* (2006.01)

(52) U.S. Cl.

CPC .......... *C09J 175/02* (2013.01); *A61K 9/7069* (2013.01)

(58) Field of Classification Search

None

See application file for complete search history.

(56) References Cited

U.S. PATENT DOCUMENTS

| | | | | |
|---|---|---|---|---|
| 5,716,661 | A * | 2/1998 | Scholz | A61L 15/125 264/131 |
| 8,378,037 | B2 * | 2/2013 | Griswold | C08G 18/289 525/452 |
| 2018/0318233 | A1 * | 11/2018 | Haddleton | A61K 9/7069 |
| 2020/0199415 | A1 * | 6/2020 | Kot | C09J 7/21 |
| 2020/0405909 | A1 * | 12/2020 | Taton | A61L 15/26 |

(Continued)

FOREIGN PATENT DOCUMENTS

WO 2020016581 A1 1/2020

OTHER PUBLICATIONS

European Search Report, Application No. 22773015.7, dated Apr. 10, 2025, 7 pages.

(Continued)

*Primary Examiner* — Randy P Gulakowski

*Assistant Examiner* — Holley Grace Hester

(74) *Attorney, Agent, or Firm* — McAndrews, Held & Malloy, Ltd.

(57) ABSTRACT

The invention relates to an adhesive composition comprising a crosslinked silyl-containing telechelic polyurea polymer and methods for making the same. Typically, the composition is formed into a patch which shows excellent adhesion to the skin even when drugs and other additives are dissolved into the composition.

8 Claims, 8 Drawing Sheets

(56) References Cited

U.S. PATENT DOCUMENTS

2021/0206900 A1* 7/2021 Chung ................ C08F 293/005

OTHER PUBLICATIONS

International Search Report and Written Opinion for PCT Patent Application No. PCT/GB2022/052261 mailed Nov. 29, 2022.
Communication Pursuant to Article 94(3) EPC, European Application No. 22 773 015.7, dated Apr. 29, 2026, 10 pages.
Polyurea in IUPAC Compendium of Chemical Terminology, 5th ed. International Union of Pure and Applied Chemistry, dated 2025, 2 pages.
Sutyagin V.M., Bondaletova L.I., Chemistry and Physics of Polymers: Tutorial—Tomski TPU Publishing House, dated 2003, 7 pages.
Brittany J. Mills et al., Effect of Linker-Drug Properties and Conjugation Site on the Physical Stability of ADCs/Hournal of Pharmaceutical Sciences, vol. 109, N.5, dated 2020, 11 pages.
Darren Pearson et al., Conjugates Toward Medicines/Journal of Pharmacology and Medicinal Chemistry, vol. 1, N.1, dated 2017, 8 pages.
Smith W. et al., Organic Synthesis. The Science Behind the Art: Translated from English.-Moscow: Mir, dated 2001, 4 pages.
Kondratieva T.S. et al., Technology of Dosage Forms: Textbook in 2 Volumes. vol. 1.-M.: Medicine, dated 1991, 4 pages.
Mashkovsky M.D., Medicines.—16th ed., revised, corr. and add.—M.: New Wave, dated 2012, 3 pages.
Ting-Chao, Drug Combination Studies and Their Synergy Quantification Using the Chou-Talalay Method/Cancer Research, vol. 70, N. 2, dated 2010, 7 pages.
Russian Office Action, Application No. 2024-515464, dated May 26, 2026, 8 pages.

* cited by examiner

PATCH

CROSS REFERENCE TO RELATED APPLICATIONS

This application claims priority to PCT Application No. PCT/GB2022/052261 having an International filing date of Sep. 6, 2022, which is incorporated herein by reference, and which claims priority to GB Patent Application No. 2112812.9, having a filing date of Sep. 8, 2021, which is also incorporated herein by reference in its entirety.

FIELD OF INVENTION

The invention relates to an adhesive composition, typically used as a transdermal drug delivery patch; a transdermal drug delivery patch comprising the composition; methods of making said composition and said patch; methods of treating diseases using the patch and the use of such compositions as pressure sensitive adhesives.

BACKGROUND

A pressure sensitive adhesive (PSA) is a material which forms a bond to a substrate when applied thereto with sufficient pressure. Such materials have a diverse range of applications. They can be used in common office applications (e.g. as sticky labels) and in more specific situations, such as for vehicle trims. However, one application of particular interest is skin patches, typically those designed for transdermal drug delivery. Patches can be pressed onto the skin and the PSA will adhere to the skin preventing the patch from falling off.

There are various requirements for such PSAs. Clearly, the adhesive must be sufficiently strong to prevent it from falling off the skin prematurely. However, it is desirable for the PSA to permit removal of the patch without causing pain (e.g. by plucking out hair or damaging the skin). Moreover, the residue left behind on the skin by many adhesives is unpleasant to users and so this also should be minimised.

Recently, PSAs have been developed which function not just as an adhesive but also as reservoirs for compounds for delivery to the skin. It has been found that some PSA compositions not only possess excellent adhesive properties but are also capable of storing large amounts of drugs. Moreover, some PSAs have shown excellent drug delivery profiles and good compatibility with a range of different drugs (with different solubility).

An example of one such PSA is shown in WO2017077284. However, in some cases, it has been found that best results are achieved when a tackifier is provided. As one skilled in the art will appreciate, the more ingredients that are introduced into a composition, the more expensive a composition becomes to manufacture. Moreover, increasing the complexity of a composition also makes it more challenging to obtain regulatory approval for compositions when used in a healthcare environment. Any additional ingredient may also decompose over time or leach out of the composition with time, altering the properties of the composition.

Adhesive compositions can be defined by the Dahlquist criterion and/or Chang's window as defined below:

Dahlquist criterion: the elastic modulus of an adhesive needs to be lower than 0.3 MPa ($3\times10^6$ dynes/$cm^2$) at 25° C. and ~1 rad/s to be able to form a good adhesive contact with a substrate.

Chang's windows: Chang proposed that the types of adhesives can be classified in four quadrants depending on the location of the viscoelastic window. Quadrant 1 (top left) is characterized by high G', low G" and corresponds to classic adhesives. Quadrant 2 (top right) is characterized by high G' and high G" and corresponds to high shear PSAs (medium peel strength, very high shear and resistance) with applications e.g., high performance tapes. Quadrant 3 (bottom left) is characterized by low G' and low G" and corresponds to removable PSAs (clean removable) for removable medical applications. Quadrant 4 (bottom right) is characterized by low G' and high G" and corresponds to cold temp. PSAs (low shear, very high peel) for e.g., labels.

It is desirable to produce a PSA which contains as few ingredients as possible but which retains the same overall adhesive and delivery properties. The invention is intended to overcome, or at least ameliorate this problem.

DETAILED DESCRIPTION

There is provided in a first aspect of the invention, an adhesive composition comprising a crosslinked silyl-containing telechelic polyurea polymer, wherein G' and G" are less than 1000 Pa at a frequency of 0.1 rad/s at 25° C.

G' and G" are measurements of rheological properties that are commonly used in the art. Rheology is the study of material deformation and flow. It can be used to establish a direct link between polymer characteristics and product performance. Rheological parameters can be measured using a parallel plate system, the shear strain (γ) and shear stress (T) are determined experimentally as follows:

$$\gamma = F\gamma\omega$$

$$\tau = F\tau T$$

where $$F\gamma\left(=\frac{R}{d}\right)$$

is the shear strain factor;

$$F\tau\left(=\frac{2}{\pi R^3}\right)$$

the shear stress factor; ω the angular displacement; T the torsional force; R the radius of the plate and d the shear gap.

The complex dynamic shear modulus (G*), storage modulus (G'), and loss or plastic modulus (G") and loss tangent (tan δ) are defined as follows:

$$|G*| = \frac{\tau}{\gamma}$$

$$G* = G' + iG''$$

$$G' = |G*|\cos\delta$$

-continued $$G'' = |G*|\sin\delta$$

$$\tan\delta = G''/G'$$

G' and G" can therefore be measured using a rheometer and standard protocols known to the person skilled in the art. The temperature and frequency at which G' and G" are measured will affect the obtained values. In this case, the values of G' and G" are obtained at a frequency of 0.1 rad/s and at 25° C. For example, the skilled person would understand that if G' and G" are measured at 0.5 rad/s and 25° C. the polymer has G' and G" values of less than 11,000.

The Inventors have found that adhesive compositions as defined above not only perform as an excellent drug reservoir and drug delivery system but also exhibit excellent adhesive properties. These properties are such that the composition can be formulated into adhesive patches without the need for additives to enhance the adhesive properties. Compositions according to the invention would also be useful as a pressure sensitive adhesive in both medical and non-medical applications where pressure sensitive adhesives have useful application. For example, in food production and packaging, electronic, and medical supplies.

In an additional or alternate aspect of the invention, the adhesive compositions has a G' and G" of less than 50,000 Pa at a frequency of 100 rad/s at 25° C.

In an additional or alternative aspect of the invention the adhesive composition of has a tan delta between 0.90 and 1.10 at at least one frequency between 0.01 and 100 rad/s at 25° C., and wherein the tan delta is not above 1.10 for any frequency between 0.01 rad/s and 100 rad/s.

As would be known by the skilled person, tan delta describes the ratio of the two portions of the viscoelastic behaviour. The following applies:

1. For ideally elastic behaviour δ=0°. There is no viscous portion. Therefore, G"=0 and with that tan δ=G"/G=0.
2. For ideally viscous behaviour δ=90°. There is no elastic portion. Therefore, G'=0 and thus the value of tan δ=G"/G' approaches infinity because of the attempt to divide by zero.

In an alternative or additional aspect of the invention, the tan delta of the adhesive composition is between 0.95 and 1.05 at at least one frequency between 0.01 and 100 rad/s at 25° C., and wherein the tan delta is less than 1.05 for any frequency between 0.01 rad/s and 100 rad/s.

In some aspects, the crosslinked silyl-containing telechelic polyurea is manufactured by a method comprising the steps of:

a) reacting a first reagent with a second reagent to form a telechelic polyurea, wherein the first reagent comprises at least one polyetherdiamine or at least one polyetherdiisocyanate, and wherein the second reagent comprises at least one diisocyanate or at least one diamine respectively; b) reacting the telechelic polyurea from step a) with a silyl containing species to form a silyl-terminated telechelic polyurea; and c) crosslinking the silyl-terminated telechelic polyurea; wherein the first reagent is provided in an excess in the range of 2 mol % to less than 100 mol % with respect to the second reagent.

Also described herein is a method for manufacturing a crosslinked sily-containing telechelic polyurea, said method comprising the steps of: a) reacting a first reagent with a second reagent to form a telechelic polyurea, wherein the first reagent comprises at least one polyetherdiamine or at least one polyetherdiisocyanate, and wherein the second reagent comprises at least one diisocyanate or at least one diamine respectively; b) reacting the telechelic polyurea from step a) with a silyl containing species to form a silyl-terminated telechelic polyurea; and c) crosslinking the silyl-terminated telechelic polyurea; wherein the first reagent is provided in an excess in the range of 2 mol % to less than 100 mol % with respect to the second reagent.

The inventors have found that by calibrating the claimed polymerisation process such that the first agent (i.e. a polyetherdiamine or polyetherdiiscoyanate) is provided in excess of the second agent (i.e. diisocyanate or diamine) the resulting composition not only performs as an excellent drug reservoir and drug delivery system but also exhibits excellent adhesive properties. These properties are such that the composition can be formulated into adhesive patches without the need for additives to enhance the adhesive properties.

For the avoidance of doubt, reference to an "excess" as used herein is in reference to a molar excess i.e. greater than a 1:1 molar ratio of the first reagent to the second reagent. Moreover, reference to an "excess" herein, for instance with respect to the first and second agent, refers to the total amount of these reagents employed in the process, with allowance for a portion of the reactive groups (e.g. amines and isocyanates) associated with a given first and second reagent being unreactive. As such, the percentage molar excess of the first reagent compared with the second reagent is calculated using the formula below:

$$((100/N_2)*N_1)-100$$

where, $N_1$ is the number of mols of the first reagent added to the reactor; and $N_2$ is the number of mols of the second reagent added to the reactor.

As one skilled in the art would appreciate, whilst diamines and diisocyanates possess two amine and two isocyanate moieties respectively, in a given sample of reagent, it is sometimes the case that a proportion of these moieties will degrade or otherwise not participate in urea formation. This percentage will be different with respect to different reagents but one skilled in the art would be able to adapt their calculations as necessary to account for this behaviour.

As one skilled in the art would appreciate, the polyurea resulting from the reaction of a polyetherdiamine and a diisocyanate is essentially identical to the polymer achieved by reacting the corresponding polyetherdiisocyanate with the corresponding diamine respectively. Both reactions form a series of urea linkages between the respective reagents.

The term "crosslinked" as used herein is intended to refer to the covalent interconnection of polymers within a composition either directly (polymer to polymer) or indirectly (polymer to intermediate bridging species to polymer) typically as a result of a reaction between particular polymer side groups (or end groups) and other corresponding side groups (or end groups) on adjacent polymers or intermediate bridging species. This may be achieved using a catalyst and/or with the presence of co-reactants, such as water. Further, elevated temperatures, radiation such as ultraviolet (UV) radiation or electron-beam (EB) radiation may be used to promote the cross-linking reaction. Where a catalyst is used, at least one catalyst is typically present in the composition in an amount in the range 0.001 to 5% by weight, more typically 0.01 to 3% by weight of the composition. The catalyst may remain in the composition or may be used up or changed in the crosslinking process. Typical examples of catalysts are crosslinking enhancers, such as titanium (IV) butoxide.

The term "curing" as used herein is to be understood as crosslinking the components of the composition together until the desired properties of the cured material are achieved. This crosslinking in the present invention typically occurs between silyl groups of the silyl-terminated telechelic polyurea described above.

Whilst it is typically the case that the telechelic polyurea formed in step a) is a linear polyurea, it is possible that some of the telechelic polyurea will be at least partially branched. As such, the polyurea may have more than two terminal groups capable of undergoing crosslinking in step c). However, it is most common for the telechelic polyurea to be linear.

The term "telechelic polymer" is intended to take its usual meaning in the art, that is to say a polymer or oligomer that is capable of entering into further polymerization or other reactions through its reactive end-groups.

It is typically the case that the diisocyanate and diamine species used as the second reagent comprise two isocyanate groups and two amine groups respectively, wherein said groups are attached to a spacer. The isocyanate groups and amine groups are typically positioned at terminal ends of said spacer. It may be that some of the diisocyanate and/or diamine include only a single isocyanate or amine group. However, the concentration of such mono-substituted species is typically low, e.g. less than 5 wt. %; more typically less than 1 wt. %.

The term "spacer" is intended to take its usual meaning in the art. In particular, it describes a moiety which provides a covalent bridge between two groups within a structure. The primary function of the spacer is to separate two groups from one another by a defined distance. The chemistry of the spacer may therefore be flexible, provided it achieves the desired spacing and does not adversely affect the reaction between the first and second reagents. Whilst there is no particular limitation on the choice of spacer, it is not typically a polymer.

Typically, the spacer is not a polyether. The spacers may be selected from: alkyl, alkenyl, alkynyl, aryl, heteroaryl each of which may be optionally substituted. Of these, alkyl, aryl and heteroaryl groups are most typically employed. Often, the spacer is an alkyl group or an aryl group. In many cases, the spacer will be an alkyl group. Said alkyl group may be $C_1$ to $C_{20}$ in length, more typically $C_2$ to $C_{15}$ and even more typically $C_3$ to $C_{10}$. Said alkyl groups may be linear, branched or cyclic alkyl. Said alkyl groups may comprise one or more heteroatom selected from S, N and O. Typical examples of spacer groups include: isophorone, phenyl or biphenyl, cyclohexyl or bicylcohexyl, and $C_2$ to $C_8$ alkyl (such as ethyl, propyl, butyl or hexyl) each of which may be optionally substituted.

The term "optionally substituted" is intended to capture those structural modifications to the species described herein that do not materially influence the functionality of the species concerned.

The diisocyanate is typically selected from: aromatic diisocyanates, aliphatic diisocyanates, or combinations thereof. As one skilled in the art will appreciate, a wide range of molecules bearing two isocyanate groups can be employed, provided that said molecules do not contain groups which disrupt the intermolecular interaction between the isocyanate groups and the amine groups present on the polyetherdiamine.

However, typical examples of diisocyanate may be selected from: isophorone diisocyanate, toluene diisocyanate, naphthalene diisocyanate, diphenylmethane diisocyanate, hexamethyl diisocyanate, bis-(4-cyclohexylisocyanate) or combinations thereof.

Similarly, the diamine is typically selected from: aromatic diamines, aliphatic diamines, or combinations thereof. As one skilled in the art will appreciate, a wide range of molecules bearing two amine groups can be employed, provided that said molecules do not contain groups which disrupt the intermolecular interaction between the amine groups and the isocyanate groups present on the polyether diisocyanate.

However, typical examples of diamines may be selected from: isophorone diamine, toluene diamine, diaminonaphthalene, diphenylmethane diamine, hexamethyl diamine, bis-(4-cyclohexylamine) or combinations thereof.

As explained above, the first reagent is provided in excess with respect to the second reagent. Often the upper limit of the excess is selected from: 95 mol %, 90 mol %, 85 mol %, 80 mol %, 75 mol %, 70 mol %, 65 mol %, 60 mol % or 55 mol %. Further, the corresponding lower limits are often selected from: 5 mol %, 10 mol %, 15 mol %, 20 mol %, 25 mol %, 30 mol %, 35 mol %, 40 mol % or 45 mol % respectively. It is often the case that the first reagent is provided in an excess in the range 5 mol % to 90 mol % with respect to the second reagent. More typically, the first reagent is provided in an excess of less than 10 mol % to 80 mol % with respect to the second reagent. Even more typically, the first reagent is provided in an excess of less than 10 mol % to 30 mol % with respect to the second reagent. In some embodiments, the first reagent is provided in an excess of less than 15 mol % to 20 mol % with respect to the second reagent. In other situations, the first reagent may be provided in an excess of less than 40 mol % to 60 mol % with respect to the second reagent.

In addition, it is often the case that the second reagent will be added to the first reagent. Further, the reaction between the first reagent and second reagent typically proceeds by combining said reagents gradually, typically in a drop wise fashion. For the avoidance of doubt, this gradual addition is typically less than or equal to 20 mol % $min^{-1}$, more typically less than or equal to 10 mol % $min^{-1}$, and in some instances less than or equal to 5 mol % $min^{-1}$. Often, the rate of addition is in the range of 1 mol % min-1 to 15 mol % $min^{-1}$; more typically 3 mol % min-1 to 12 mol % $min^{-1}$; and most typically 5 mol % min-1 to 10 mol % $min^{-1}$.

Moreover, it is often the case that the second reagent is added to the first reagent in a series of steps. Accordingly, a first amount of the second reagent can be added to the first reagent and allowed to react until substantially no further second agent is present. Following this, a subsequent second amount of the second reagent may be added to the reaction mixture. This process can be repeated multiple times, such that the method involves in the range of 1 to 10 additions, more typically 2 to 8 additions, even more typically 3 to 6 additions and often 4 or 5 additions. This kind of addition is referred to herein as "step-wise" addition. This is not to be confused with steps a) to c) also referred to herein, which characterise different stages in the polymer production process. It may be that the amount by mass of second reagent present in each subsequent addition is less than a previous addition. In some cases, the subsequent amount by mass is approximately half that used in the previous amount of the second reagent. As one skilled in the art will appreciate, each addition of second reagent promotes further chain extension, reducing the number of moles of the polymeric intermediate formed in the previous step. Said polymeric intermediate then forms the basis to which a further tranche of a second reagent can react. For the avoidance of doubt, the first reagent is provided in excess of the sum total of second reagent used in all steps, where a staged addition is employed. Each step is typically allowed to proceed substantially to completion. This can be monitored in a number of ways that would be familiar to one skilled in the art, such as by dynamically monitoring the disappearance of characteristic signals in the spectra of test samples.

As explained above, the first reagent is either a polyetherdiamine or a polyether diisocyanate. Typically, first reagent possesses a weight average molecular weight in the range 2000 Da to 10,000 Da. Often, the first reagent possesses a weight average molecular weight in the range 2500 Da to 8000 Da; more typically, a weight average molecular weight in the range 3000 Da to 6000 Da; and most typically, a weight average molecular weight in the range 3500 Da to 5000 Da.

Both the polyetherdiamine and the polyether diisocyanate comprise a polyether moiety, terminated at both ends with amine and isocyanate groups respectively. Usually, the polyether moiety has a structure according to formula (I)

(I)

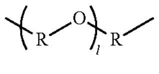

wherein R is selected from: alkyl, alkenyl, alkynyl, aryl, heteroaryl, each of which may be optionally substituted; and I is an integer in the range of 2 to 100. Typically, R is an alkyl or alkenyl, more typically an alkyl. Usually, R is a small group, with a length in the range of $C_1$ to $C_{10}$, more typically $C_1$ to $C_8$, even more typically $C_2$ to $C_6$, and in some cases $C_2$ to $C_4$. Usually, R is a $C_1$, $C_2$ or $C_3$ group, most typically either a $C_2$ or a $C_3$ group. Often, R is selected from methyl, ethyl, propyl and butyl, more typically ethyl or propyl.

Moreover, whilst it is often the case that only a single type of ether monomer is used in the polyether moiety, various different monomers may additionally be employed. For example, a mixture of different ether monomers could be used to fabricate a polyether moiety containing different ether monomer units within its structure. The polyether moiety may be a copolymer comprising one or more blocks of polyether sub-units and/or addition polymer sub-units. Accordingly, alternating copolymers and block copolymers are also envisaged as suitable polyethers moieties. For example, the polyether moiety may include a poly(propylene glycol) portion and a poly(ethylene glycol) portion. Alternatively, the polyether moiety could be a copolymer fabricated from a mixture of ethyl ether and propyl ether monomers so as to form an alternating copolymer of these two monomers.

In some instances, the polyether moiety is selected from: polyoxymethylene, poly(ethylene glycol), poly(propylene glycol), poly(1,2-butylene glycol), poly(tetramethylene glycol), or combination thereof. Of these, poly(ethylene glycol) and poly(propylene glycol) or combinations thereof are most typically employed. Reference to "combinations thereof" as used herein is intended to embrace both copolymers and blends of polymers. Whilst the polyether is typically fabricated from exclusively ether monomers (most typically ethylene glycol and/or propylene glycol), the polyether moiety may additionally comprise non-ether monomers in its structure. The concentration of these monomers in the polyether are usually comparatively small compared to the ether monomers. Typically, the concentration of non-ether monomers present in the polyether moiety is less than or equal to 20% mol, more typically less than or equal to 10% mol, even more typically less than or equal to 5% mol, and commonly less than or equal to 1% mol. In some embodiments, the polyether moiety is exclusively formed from ether monomers. In addition to the diisocyanate or diamine described above, the second reagent may also further comprise one or more additional diisocyanates or diamines. As one skilled in the art will appreciate, introducing a further monomer into the process, bearing either isocyanate groups or amines groups, will cause that monomer to be inserted into the resulting telechelic polyurea. These monomers will insert themselves into the structure of the telechelic polyurea.

Although the telechelic polyurea formed in step a) can be fabricated using either a polyetherdiamine or a polyether diisocyanate as the first reagent, it is typically the case that the first reagent is a polyetherdiamine. Accordingly, it is typically the case that the second reagent is a diisocyanate.

It is often the case that the method of the first aspect of the invention is performed without solvent. It is possible in many circumstances that first and/or second reagent can act as both reagents and solvents, removing the necessity for a separate solvent. This is especially valuable when fabricating compositions for use in medical applications due to the strict regulations imposed on such products, where even small levels of impurities can prevent approval.

The process in steps a) and b) at least typically do not require a catalyst.

The process of the first aspect of the invention is not limited to any particular temperature. However, as one skilled in the art would appreciate, the kinetics of polymerisation reactions (like most chemical reactions) are partially governed by the temperature of the process. Accordingly, it is typically the case that the temperature of the process is in the range 5° C. to 150° C. and more typically 10° C. to 100° C. In some embodiments, the process may be conducted at room temperature (such as, in the range of 15° C. to 30° C.).

In order to form the crosslinked silyl-containing polyether polyurea, the silyl-terminated telechelic polyether polyurea formed in step b) must be cured, so as to connect the silyl groups of adjacent silyl-terminated telechelic polyether polyurea molecules together. Numerous methods exist for promoting such reactions such as radiation curing, thermal curing and moisture curing. Each of these processes may employ a suitable catalyst. However, it is typically the case that the telechelic polyurea is moisture cured.

The polymerisation reaction of step a) can be terminated by beginning step b) i.e. introducing a silyl-containing species which will react with the terminal amine or isocyanate at the end of the propagating chain. The silyl containing species is typically an amine or alcohol (where it is intended to react with a terminal isocyanate); or an isocyanate (where it is intended to react with a terminal amine). Whilst the amine is usually a primary amine, secondary amines are also contemplated. Usually, a silyl-containing species is reacted so as to create silyl groups on each of the terminal ends of the polyurea. In many circumstances, the silyl-containing species has a formula according to formula (II)

(II)

$$A—L—R^5$$

wherein $R^5$ comprises a silyl group;

A is either an amine, alcohol or an isocyanate; and

L is an optional linker or bridging group.

As one skilled in the art would appreciate, a linker or bridging group connects the two groups together. For the avoidance of doubt, this linker is optional as a single bond could also directly bind A and $R^5$ together. There are no real limitations on the identity of the linker provided it does not compromise the chemistry of the silyl-containing species. Typically, L is selected from: alkyl, alkenyl, alkynyl, aryl, heteroaryl each of which may be optionally substituted. Typical examples of linkers include alkyl and aryl groups and usually the linker is short, usually in the range of $C_1$ to $C_{10}$.

$R^5$ typically has a structure according to formula (III)

$$—Si(R^6)_j(OR^6)_{3-j} \quad \text{(III)}$$

wherein $R^6$ is independently selected from: alkyl, alkenyl, alkynyl, aryl, heteroaryl each of which may be optionally substituted; and j is an integer in the range of 0 to 2. In some situations, j is 1 or 2. Most typically, $R^6$ is independently an alkyl group, typically a $C_1$ to $C_6$ alkyl group. Of these, butyl, propyl, ethyl and methyl are preferred. Often, $R^6$ is independently be either ethyl or methyl; and often $R^6$ is methyl.

Often, the method for making the crosslinked silyl-containing telechelic polyurea is performed without a solvent. One of the advantages of the method is that the reagents themselves can function as the solvent for the reaction. This is advantageous from a commercial perspective, as the process requires fewer ingredients, but also from a structural perspective as residue solvent is not incorporated into the crosslinked polyurea during the curing process.

It may be the case that, after the silyl group has been applied to the polyurea, residual silylating agent is present in solution. This can cause problems in downstream applications and so, it is often the case, that the process includes a step of removing this residual silylating agent. A variety of agents can be employed to achieve this removal and the choice of compound used will vary depending on the particular choice of silylating agent employed. For instance, a common silylating agent that may be used in the present invention is (3-isocyanopropyl) trimethoxysilane, often abbreviated to "IPTMS". To remove an excess of IPTMS, a typical compound would be (3-aminopropyl) trimethoxysilane, often abbreviated to APTMS. These two compounds react to form a terminally silylated species that can also be crosslinked in step b). Such a process is typically performed before step c) but after step b).

The method for producing the crosslinked silyl-containing telechelic polyurea is typically conducted at a temperature in the range of 10° C. to 100° C. More typically, the temperature is in the range 40° C. to 90° C., and more typically 50° C. to 75° C. At temperatures lower than this the rate stirring the mixture is lower than optimal, and at higher temperatures the energy consumption begins to become less commercially practical.

The curing process employed in the invention, (step c) above) is not particularly limited. As one skilled in the art will appreciate, a number of techniques exist to bring about the crosslinking of the silyl groups so as to form a matrix of interlinked silyl containing polymer chains. For instance, the curing process may use radiation curing or moisture curing. The choice of curing often depends upon the choice of materials incorporated into the crosslinked polymer. For instance, where the composition is used for drug delivery, if the drug to be delivered is not thermally stable (and so not capable of undergoing a practical moisture curing process) a radiation cure method may be employed. Conversely, if an additive is not radiation stable, a moisture curing method will be employed. Typically, though, it is the case that a moisture curing process will be used. Such processes would be familiar to one skilled in the art.

It is often the case that the silyl-containing un-crosslinked polyurea formed in the process of the invention possess a viscosity (when measured at 80° C.) in the range 2,000 cP (centipoise) to 55,000 cP; more typically 4,000 cP to 45,000 cP; even more typically, 8000 cP to 40,000 cP; and most typically 15,000 cP to 35,000 cP, as measured using a rotational viscometer, such as a Brookfield viscometer.

There is also provided in a second aspect of the invention, an adhesive composition comprising a crosslinked polyurea obtained by the process according to the first aspect of the invention.

The inventors have discovered that, the adhesive compositions of the invention have excellent transdermal drug delivery properties and also display excellent adhesive properties as a PSAs. Indeed, the properties of such crosslinked polyureas are at least comparable to those polymeric compositions in the prior art that employ tackifying agents (see for instance those identified in WO 2017/077284, pages 40 to 44).

It is often the case that each of the crosslinked silyl-containing telechelic polyurea comprises a structure according to formula (IV):

(IV)

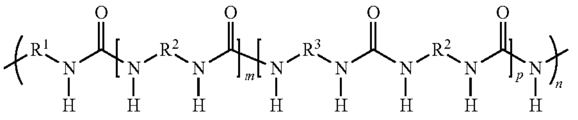

wherein $R^1$ is a polyether as defined previously;

$R^2$ is a spacer as defined previously;

$R^3$ is a spacer or polyether;

n is an integer in the range of 1 to 100;

m is an integer in the range 0 to 1;

and p is an integer in the range 0 to 10;

wherein the sum of m and p>0.

It is often the case that $R^3$ is different from both $R^1$ and $R^2$. Typically, p is 0 or 1; most typically p is 0. Moreover, it is often the case that m is 1. Usually, $R^3$ is a spacer. Further, n is typically in the range of 5 to 90; more typically 10 to 80; and even more typically 20 to 70.

As explained above, by preparing the polymers using the method according to an aspect of the invention, a mixture of polyureas is formed which produce a composition with excellent physical properties for use in transdermal drug delivery devices. The polyurea typically comprises this structure, that is to say, this structure exists within the polyurea.

Usually, the crosslinked silyl-containing polyurea comprises a structure according to formula (V):

(V)

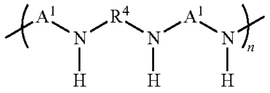

($A^1$)

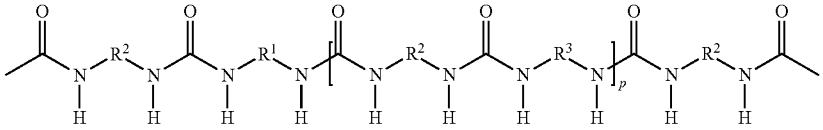

wherein $R^1$, $R^2$, $R^3$, n and p are as described above; and wherein $R^4$ is a spacer;

wherein $R^4$ is different to $R^1$, $R^2$ and $R^3$.

Often, it will be the case that the silyl-terminated telechelic polyurea has a structure according to formula (VI):

typically possess the same functionality as the polymers of the invention. In the present invention, the adhesive properties of the crosslinked polymers alone are sufficient for a variety of PSA applications. Therefore, an additional tackifier is not required. Typical tackifiers include tackifying (VI)

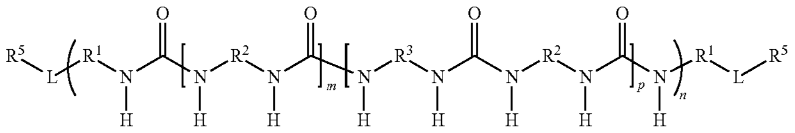

wherein $R^1$, $R^2$, $R^3$, $R^5$, n, m and p are as described above.

Often, the silyl-terminated telechelic polyurea has a structure according to formulae (VII) or (VIII):

resins. Examples of tackifying resins include, but are not limited to, phenol modified terpene resins (typically polyterpenes), hydrocarbon resins (typically where the hydro- (VII)

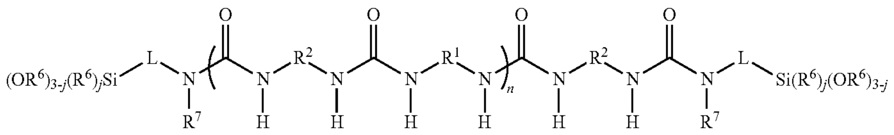

(VIII)

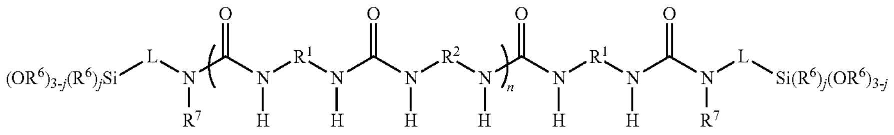

wherein $R^1$, $R^2$, L, $R^6$, $R^7$, n and j are as described above wherein $R^8$ is selected from: hydrogen, alkyl, alkenyl, alkynyl, aryl, heteroaryl each of which may be optionally substituted. Most typically $R^4$ is hydrogen or a $C_1$ to $C_8$ alkyl; more typically hydrogen, methyl or ethyl; and most typically hydrogen.

It is typically the case that the composition is a pressure sensitive adhesive (PSA). As one skilled in the art will appreciate, a pressure sensitive adhesive is a non-reactive adhesive which forms a physical bond to a surface when pressure is applied to it.

Often, the composition is substantially free of a tackifier. The term "substantially free" typically means that less than 5% by weight of the composition will be a tackifier. More typically, less than 3% by weight of the composition will be a tackifier, often less than 2% and most often less than 1%. Usually, no tackifier is present. The term "tackifier" is intended to describe a composition which modifies the tackiness of a composition, typically imbuing a composition with enhanced adhesive properties. The tackifier does not carbons have an aromatic character, i.e. comprise one or more aromatic groups), rosin ester resins, modified rosin ester resins and acrylic resins.

In addition, the ability to remove tackifiers and like components means that more favourable processing temperatures can be employed. Further, with fewer ingredients present in the composition, the profile of leachable compounds (such as drugs, for example) is cleaner as there are fewer ingredient capable of being leeched.

Typically, the pre-cured composition has a viscosity (when measure at 80° C.) in the range 1,000 to 55,000 cP; more typically 6,000 to 40,000 cP; and, even more typically, 8,000 to 35,000 cP. In some embodiments, the viscosity of the composition may be lower than that of the silyl-containing un-crosslinked polyurea.

Moreover, it is typically the case that the composition is substantially free from plasticisers. That said, other types of additive may be employed. Additional additives may be introduced into the composition as would be familiar to a person skilled in the art such as permeation enhancers (i.e.

species that modify the ability of drugs to travel across the skin barrier), pH modifiers and surfactants provided that said additional components do not interfere with the drug delivery properties or the adhesive properties of the composition. Typical examples of permeation enhancers include, but are not limited to: propylene glycol, diethyleneglycol ethyl ether, dimethyl sulfoxide, ethanol, octadecanol, and combinations thereof.

In some embodiments, the composition is substantially free from antioxidants.

There is also provided in an aspect of the invention, a transdermal drug delivery patch comprising the composition of the second aspect of the invention, wherein the composition comprises one or more drugs suitable for transdermal drug delivery. The inventors have found that these compositions function well as both a reservoir and a means of delivery for transdermally deliverable drugs, as well as providing excellent adhesive properties.

The term "drug" as used herein is intended to refer to a biologically active substance. There is no particular limitation on the type of compound from which the drug is made. The drugs used with the present invention are typically small molecule drugs. However larger molecules and macromolecules are also envisaged including biological compounds such as peptides and proteins. The term "drug" is also intended to encompass pharmaceutically acceptable salts of biologically active substances. It is also envisaged that the drug may provide a physical effect on the body, such as heating or cooling, which may have a therapeutic effect. The term "drug" is also intended to encompass compounds useful for well-being such as: vitamins, nutraceuticals, menthol, capsaicin, cannabidiol (CBD) and the like. Such compounds do not necessarily treat a disease as such, but are useful in maintaining health.

The term, "small molecule drugs" is intended to encompass those compounds typically produced by synthetic chemical processes having a molecular weight typically less than 1000 Da, more typically less than 700 Da, and most typically less than 500 Da.

Typically, the patch comprises: a substrate; and a layer of the composition according to the second aspect of the invention applied to the substrate, wherein the composition comprises one or more drugs for transdermal drug delivery. The substrate typically comprises a surface which is not adhesive and which allows the patch to be manipulated by the user. Typically, the substrate is a backing liner. As one skilled in the art would appreciate, a backing liner is a layer of material to which the operative components of the patch are applied. In the present case, the backing liner provides a non-adhesive surface that allows the patch to be manipulated. Typically, the backing liner is substantially non-porous i.e. it prevents compounds from the composition from leeching out through the backing layer. The backing liner can also provide structural support to the patch to ensure the patch retains its shape or at least resist undue structural deformation. However, non-porous backing liners are also contemplated and, in some embodiments, it is advantageous for the backing liner to be made from a flexible material, such as a stretchable fabric.

Usually, the patch comprises: a backing liner; a release liner; and a layer of the composition according to the second aspect of the invention, wherein the composition comprises one or more drugs suitable for transdermal drug delivery. As one skilled in the art will appreciate, a release liner is a layer of material which sandwiches the operative components of the patch between itself and the backing liner. The release liner also includes a surface which is not adhesive such that the patch can be easily manipulated prior to use. The release liner is typically made from a material that can be detached cleanly from the operative layer of the patch, exposing the adhesive operative layer for attachment to a user. Therefore, the adhesive qualities of the release liner are typically low so as to ensure easy removal but sufficient to ensure retention of the layer in position prior to use. The backing liner and the release liner are adjacent the layer of composition but one or more intermediate sheets of material may be positioned between the backing liner and the layer of composition and/or between the release liner and the layer of composition. However, it is often the case that the backing liner and the release liner are directly adjacent the layer of composition. There is no particular method or order for the assembly of the patch. However, often the composition will be applied to the release liner, which is then subsequently attached to the backing liner.

There is no particular restriction on the choice of drug that may be included in the patch of the invention. However, it is typically the case that the drugs used are hydrophobic. Typical examples of hydrophobic drugs include apomorphine, artemisinin, artesunate, aspirin, azathioprine, azelastine, bisoprol, buprenorphine, calitrol, calciferol, cannabinoids, capsaicin, carbamazepine, cetirizine, chlorhexidine, clobetasone butyrate, clonidine, clotrimazole, cyclosporine, desloratadine, dexamethasone, dicflucortolone valerate, diclofenac epolamine, ergotamine, donepezil, β-estradiol, fenbufen, fentanyl, flurbiprofen, gestodene, hydrocortisone, ibuprofen, indomethacin, iodine, ivermectin, ketoprofen, lamotrigine, levomenthol, levonorgestrel, loratidine, melatonin, naproxen, norelgestromin, norethisterone, penicillin, piroxicam, pramipexole, praziquantel, prednisolone prilocaine, progesterone, propylthiouracil, quinidine, risperidone, salbutamol, methyl salicylate, salsalate, saquinavir, simvastatin, teriparatide, testosterone, tetrabenazine, triamcinolone, trimethoprim and varenicline.

Alternatively, the drug may be hydrophilic. Typical examples of hydrophilic drugs include acyclovir, allopurinol, amoxicillin, caffeine, ceftriaxone, cisplatin, cyclophosphamide, dopamine, dopamine hydrochloride, doxycycline, fluloxetine, fluorourcil, gabapentin, gentamycin, lamivudine, lidocaine, methotrexate, nicotine, nystatin, paracetamol, penicillamine, silver nitrate, sufentanil citrate, temozolomide, tetracycline and triamcinolone. It may be the case that the drug is lidocaine. It is also envisaged that the drug comprises one or more cannabinoids.

The drug is typically present in the composition in an amount in the range of 0.1% to 40% by weight of the composition, more typically 1% to 35%, even more typically 5% to 30% by weight of the composition, more typically still 8% to 20% by weight of the composition, even more typically 10% to 15% and often representing about 12.5% by weight of the composition.

In an aspect of the invention, there is provided a pressure sensitive adhesive comprising the composition according to the first aspect of the invention. Whilst one preferred embodiment relates to transdermal drug delivery, the composition of the second aspect of the invention is itself useful as a pressure sensitive adhesive. Accordingly, the composition of the second aspect of the invention may be employed in a diverse array of applications requiring PSAs. Typical applications include, but are not limited to: glues, labels, tapes, protective films, medical devices (such as EKG monitors and wound care dressings), skin patches i.e. patches that may not contain active pharmaceutical agents (but may contain agents designed to provide a range of physical effects, such as heating or cooling sensations), note pads, automobile trims, and the like.

In a further aspect of the invention, there is provided a method of treating a disease, comprising the step of applying the patch according to the third aspect of the invention to a user. There is no particular limitation on the types of disease that can be treated using this method. The only limitation is that the drugs used to treat a particular condition are effective when administered to the skin. Typical applications for the composition of the invention include the treatment of diseases selected from: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof.

Further, the method of treatment of the invention may also be for delivering vaccines and/or for improving wound healing.

There is also provided in an aspect of the invention a composition or patch for use in therapy. Typically, the conditions which can be treated with the composition or patches of the invention are: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof. Most typically, the compositions and patches of the invention are for use in treating analgesia. Further, the composition and patches of the invention may also be used as a means for delivering vaccines and/or as a means to improve wound healing.

Any numerical value provided herein is intended to be modified by the term "about". Further, the disclosure of a range is intended to disclose the range, the specific values between the limits of the range and especially the integers between said limits.

In addition, although features may be described as "comprising" part of the invention, all the features described herein may also be considered as "consisting of" or "consisting essentially of" part of the invention.

EXAMPLES

Figure 1:
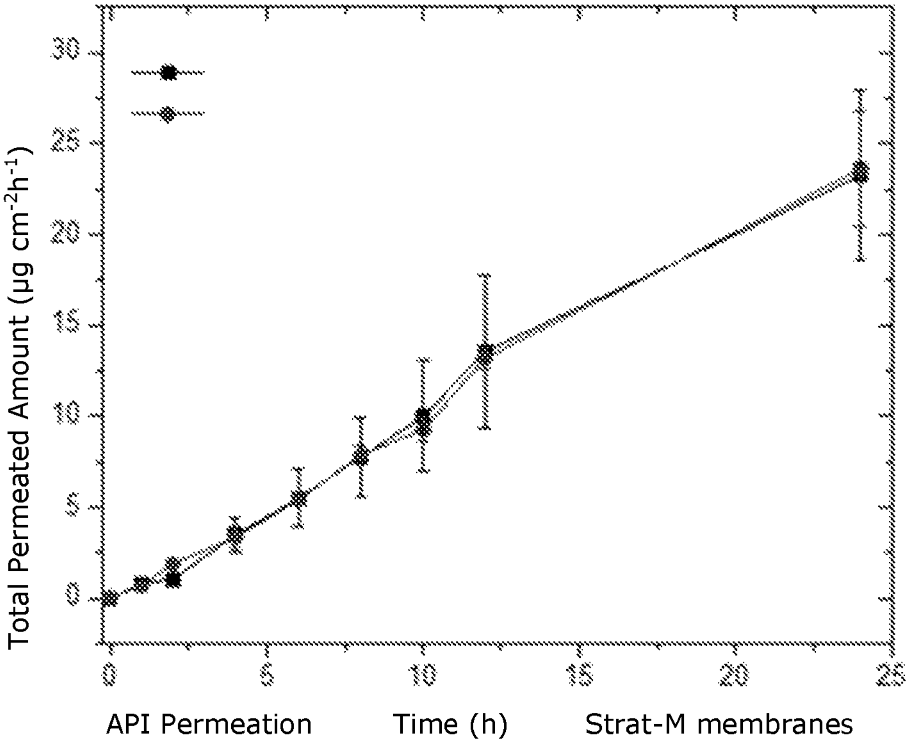
FIG. 1 shows—Permeation of cannabidiol (CBD) through synthetic membranes (Strat-M) from formulations F14 and F3 with cannabidiol.

Scheme 1 shows an exemplary embodiment of a method for making a polymer according to the invention. A diisocyanate is added to a polyether diamine in a gradual fashion in step i) in order to exclusively form a first diamine intermediate. That intermediate can then be reacted again in step ii) with more of the diisocyanate, again in a gradual fashion to exclusively create a second intermediate. Step ii) can be repeated numerous times where, each time, the diamine products of the previous step serve as the starting material to which the diisocyanate is added. As such, the value of k theoretically increases by a factor of two plus 1 each time step ii) is repeated. In other words, if the starting k value is $k_1$ and the new k value is $k_2$, one could state that $k_2$ is approximately equal to $2k_1+1$. If k grows too large, i.e. around 100 or 150 for example, this is less desirable as the polymers often become too viscous to be practically useful. The total amount of diisocyanate added in each step is reduced by around half each time as the number of moles of intermediate each time is reduced as precursor diamines from previous steps are incorporated into the structure of subsequent diamines.

Finally, in step iii), the propagation of the polymer is terminated through the addition of a trimethoxylsilyl isocyanate. In Scheme 1 poly(propylene glycol) diamine, toluene diisocyanate and trimethoxylsilyl propyl isocyanate are used to illustrate the process.

Scheme 1. Example Process for the Production of a Silyl-Terminated Polyurea

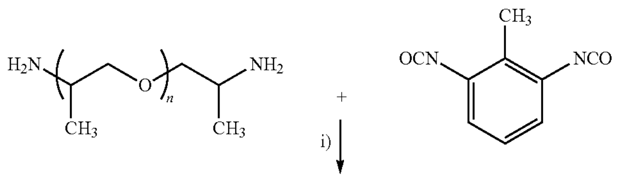

-continued

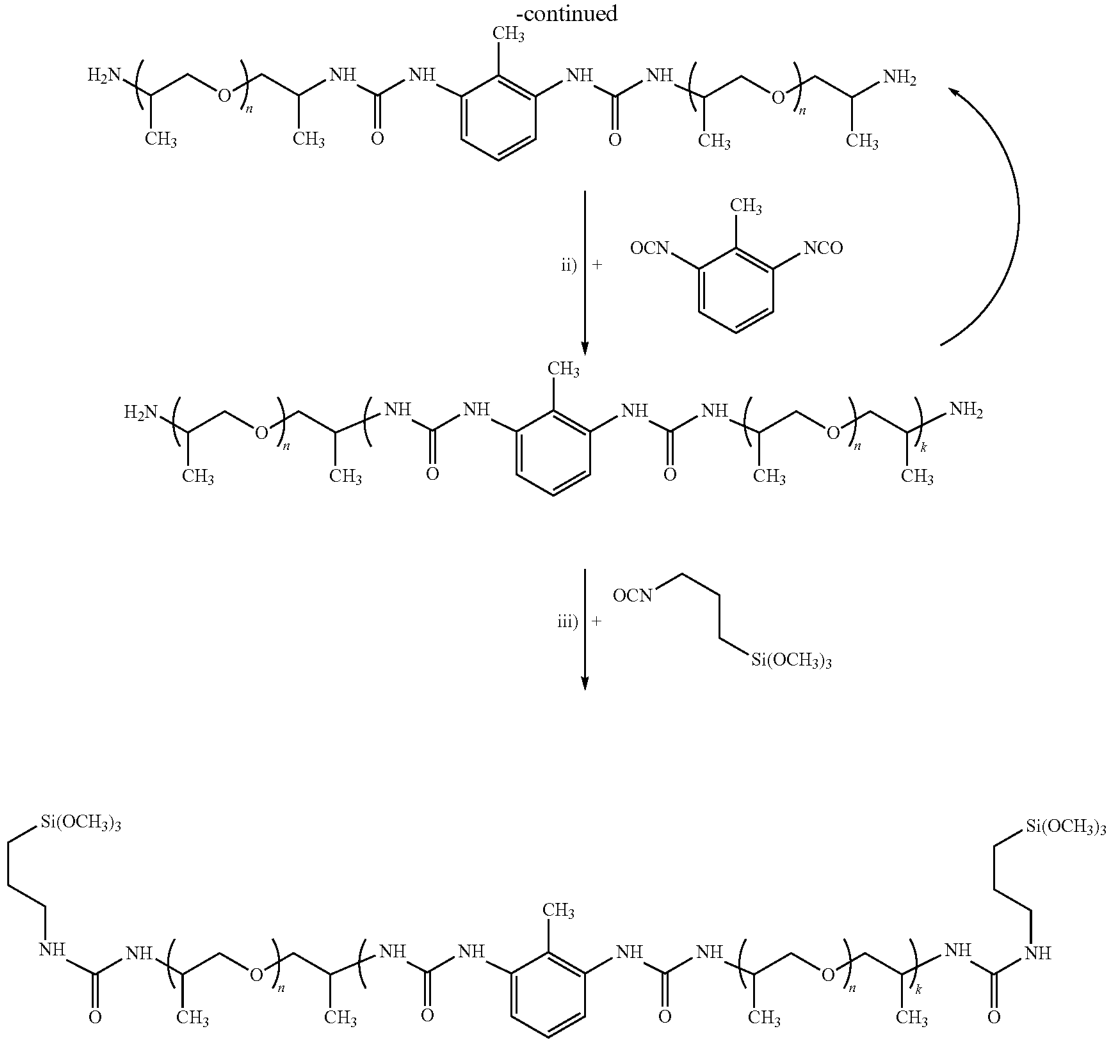

As can be seen from Scheme 1, the polyurea of the invention is synthesised in various stages. The adhesion properties of the different versions of the PSA were compared using two adhesion tests, 90° peel and loop tack. The polymers of the invention were compared with existing polymer patch technology that require tackifiers in their formulation. Results are shown in the tables below.

Scheme 2. Alternative Process for the Production of a Silyl-Terminated Polyurea

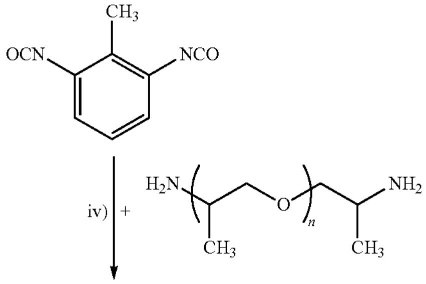

-continued

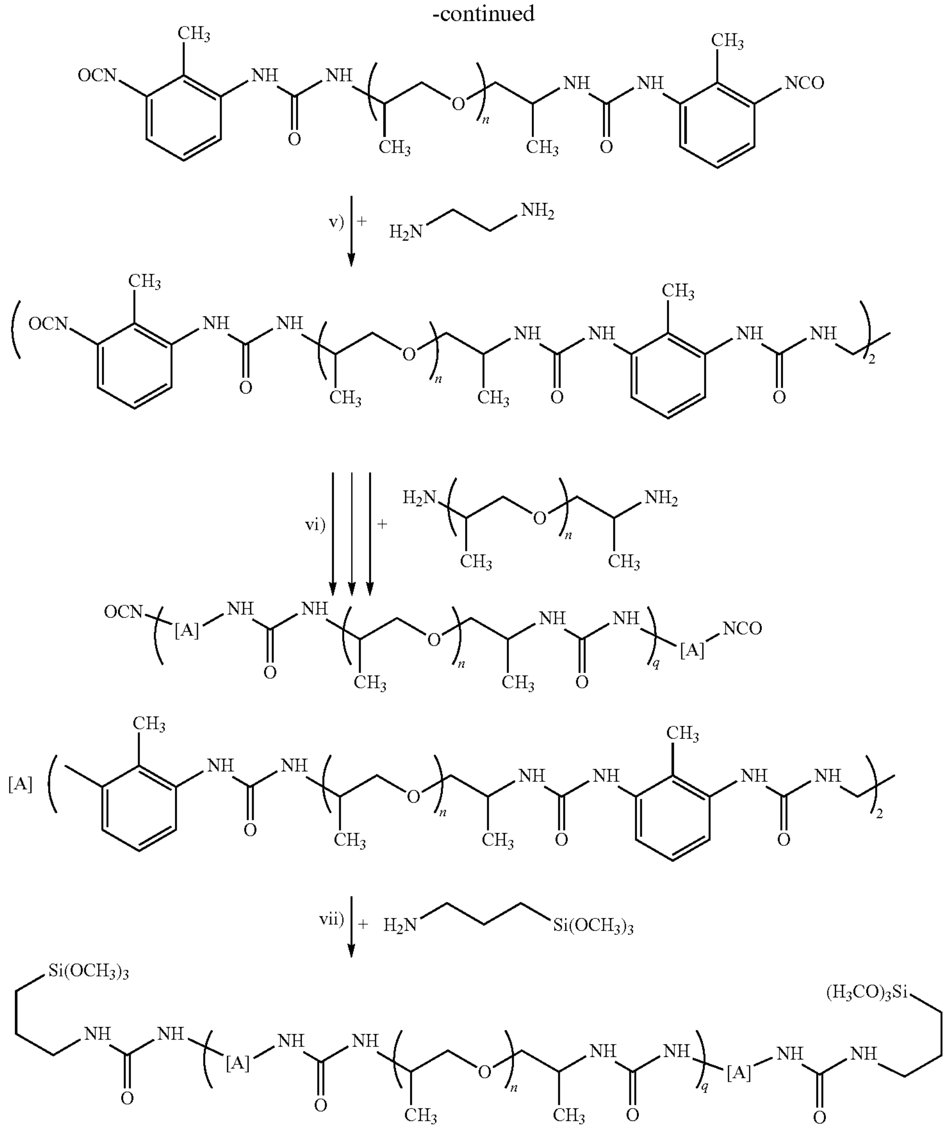

The process shown in Scheme 2 is an alternative method wherein a diamine is added to the diisocyanate. The same exemplary agents from step i) of Scheme 1 have been used in step iv). However, step v) introduces an ethyl group into the polymer structure using an ethylenediamine monomer. The resulting diisocyanate is then reacted with further amounts of the diamine from step iv) in multiple step-wise additions in step vi). The number of step-wise additions performed in step vi) determines the number average integer value of q. Finally, the polymer propagation is terminated using trimethoxylsilyl propyl amine.

Example 1—Production of Silyl-Terminated Polyurea

To a vessel of 4707.67 g of polyetheramine (Jeffamine D-4000™, a polyoxypropylene diamine), 124.26 g of isophorone diisocyanate was added whilst stirring at a temperature of 75° C. The solution was continuously mixed and sampled to monitor the —NCO bond concentration until it was no longer detected. Once no further isocyanate was detected, the step was repeated by addition of a further 59.02 g of isophorone diisocyanate and reacted until no further isocyanate was detected. This process was repeated twice more with 28.04 g and 13.32 g of isophorone diisocyanate respectively at each subsequent step. Once all diisocyanate had been reacted, 64.86 g of 3-isocyanatopropyl trimethoxysilane was added to the reaction vessel and left to react to form the silyl-terminated polyurea. 2.83 g of (3-aminopropyl) trimethoxysilane is added to react with any residual isocyanate species.

By way of contrast, table 1 shows polymer compositions wherein the silyl-terminated polyurea is made by the above method but without an excess of polyetheramine and wherein only a single addition of isophorone diisocyanate is employed.

The percentage molar excess of the first reagent compared with the second reagent is calculated using the formula below:

The formula for a single addition of isophorone diisocyanate or for every first step of isophorone diisocyanate addition is:

$$n_{IPDI\,Step,1} = \left(\frac{m_{polyetheramine} \times A_T \times 0.5)}{1000}\right) \times 0.5 \times 0.95$$

For the rest Steps when required the moles of isophorone diisocyanate are calculated as:

$$n_{IPDI\,Step,x} = \left[n_{IPDI_{Step,x-1}} \times 0.5 \times 0.95\right] / 222.28$$

where $m_{polyetheramine}$-mass of polyetheramine added into the vessel, $A_T$—total amine content of polyetheramine used provided in the material's certificate of analysis.

Example 2—Production of Adhesive Composition without Tackifiers (F1)

To a vessel containing 9.9 g of the silyl terminated polyurea of Example 1, 0.1 g of titanium (IV) butoxide was added. The mixture was heated to 55° C. and cast on a PET substrate as a thin film of 130 micron by passing under a heated blade. The film was kept at a temperature of 80° C. for 6 minutes in a humid atmosphere, with greater than 50% relative humidity. The thin layer of liquid polyurea cross-linked into the form of a pressure sensitive adhesive.

Example 3—Production of Adhesive Composition with Tackifiers (F2)

A vessel containing 19.8 g Arakawa KE311 tackifying resin was heated to 120° C. under a nitrogen atmosphere. To the heated resin 79.2 g of the silyl terminated polyurea of Example 1 was added and left stirring at 120° C. for 3 hours until the mixture was homogenous. The vessel was then cooled to 80° C. 1 g of titanium (IV) butoxide was added and the solution was cast on to a PET substrate as a thin film of 130 micron by passing under a heated blade. The film was kept at a temperature of 80° C. for 6 minutes in a humid atmosphere, with greater than 50% relative humidity. The thin layer of liquid polyurea crosslinked into the form of a pressure sensitive adhesive.

Example 4—Production of Adhesive Composition with Tackifiers (F3)

A vessel containing 39.6 g Arakawa KE311 tackifying resin was heated to 120° C. under a nitrogen atmosphere. To the heated resin 59.4 g of the silyl terminated polyurea of Example 1 was added and left stirring at 120° C. for 3 hours until the mixture was homogenous. The vessel was then cooled to 80° C. 1 g of titanium (IV) butoxide was added and the solution was cast on to a PET substrate as a thin film of 130 micron by passing under a heated blade. The film was kept at a temperature of 80° C. for 6 minutes in a humid atmosphere, with greater than 50% relative humidity. The thin layer of liquid polyurea crosslinked into the form of a pressure sensitive adhesive.

Example 5—Production of Adhesive Composition with Tackifiers (F4)

A vessel containing 49.5 g Arakawa KE311 tackifying resin was heated to 120° C. under a nitrogen atmosphere. To the heated resin 49.5 g of the silyl terminated polyurea of Example 1 was added and left stirring at 120° C. for 3 hours until the mixture was homogenous. The vessel was then cooled to 80° C. 1 g of titanium (IV) butoxide was added and the solution was cast on to a PET substrate as a thin film of 130 micron by passing under a heated blade. The film was kept at a temperature of 80° C. for 6 minutes in a humid atmosphere, with greater than 50% relative humidity. The thin layer of liquid polyurea crosslinked into the form of a pressure sensitive adhesive.

90° Peel Test on a Stainless Steel Plate 20 Minutes:

The adhesive strength is evaluated by the 180° peel test on a stainless steel plate as described in FINAT method No. 1 published in the FINAT Technical Manual, $6^{th}$ edition, 2001. FINAT is the international federation for self-adhesive label manufacturers and converters. The principle of this test is the following.

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% relative humidity atmosphere. It is then fastened over two-thirds of its length to a substrate constituted of a stainless steel plate. The assembly obtained is left for 20 minutes at room temperature. It is then placed in a tensile testing machine capable, starting from the end of the rectangular strip that is left free, of peeling or debonding the strip at an angle of 90° and with a separation rate of 300 mm per minute. The machine measures the force required to debond the strip under these conditions.

Loop Tack Test

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% relative humidity atmosphere. The 2 ends of this strip are joined so as to form a loop, the adhesive layer of which is facing outward. The 2 joined ends are placed in the movable jaw of a tensile testing machine capable of imposing a rate of displacement of 300 mm/minute along a vertical axis with the possibility of moving back and forth. The lower part of the loop placed in the vertical position is firstly put into contact with a horizontal glass plate measuring 25 mm by 30 mm over a square area measuring around 25 mm per side. Once this contact has occurred, the displacement direction of the jaw is reversed. The tack is the maximum value of the force needed for the loop to be completely debonded from the plate.

Rolling Ball Tack Test

The tackiness of patches was determined utilising a ChemInstruments RBT-100 ramp that meets PSTC-6 test method standards. A ball bearing was used as the test substrate. Samples were cut to give a 150 mm×25 mm test area and the distance travelled by the ball along the strip was recorded. An average of three measurements (n=3) was accepted as a statistically robust value of adhesion.

Viscosity

Viscosity of compositions was determined using a Brookfield viscometer utilising spindle number 27 and a Thermosel. the composition at 80° C. was added to a preheated crucible, 10.5 g for each measurement were required. Measurements were recorded by the instrument every minute for ten minutes. The test was repeated until concordant results were observed. The average of these ten concordant results were reported as the viscosity value for the measured batch.

Rheology Analysis

Rheological analysis was performed on an Anton Parr MCR 302 rheometer using a measuring parallel plate configuration (diameter of 25 mm) at 25° C. For all oscillatory sweep experiments, cured adhesive discs of 25 mm diameter were used. Amplitude sweep measurements were carried out using a strain (%) range of $\gamma$=0.01-710% at a constant angular frequency of $\omega$=10 rad/s. Frequency sweep experiments were conducted at an angular frequency range of $\omega$=0.5-100 rad/s and at a constant strain (%) of $\gamma$=1.0%. An average of at least three measurements (n=3) was accepted as a statistically robust run.

TABLE 1

Formulations containing tackifiers

| | Excess Amine, mol % | Silylated Polyurea, wt % | Tackifiers, wt % | 90° peel, N/25 mm | Loop tack, N | Viscosity at 80° C., cP |
|---|---|---|---|---|---|---|
| F1 | 100 | 100 | 0 | 2.0 | 0.16 | 2600 |
| F2 | 100 | 80 | 20 | 1.6 | 0.26 | 3300 |
| F3 | 100 | 60 | 40 | 3.7 | 4.01 | 4000 |
| F4 | 100 | 50 | 50 | 13.9 | 7.13 | 6000 |
| F5 | 100 | 40 | 60 | 31.8 | 14.61 | 9900 |
| F6 | 100 | 20 | 80 | 0.5 | 0.01 | 56500 |
| F7 | 100 | 45 | 55 | 30.9 | 11.3 | 5400 |

TABLE 1-continued

Formulations containing tackifiers

| | Excess Amine, mol % | Silylated Polyurea, wt % | Tackifiers, wt % | 90° peel, N/25 mm | Loop tack, N | Viscosity at 80° C., cP |
|---|---|---|---|---|---|---|
| F8 | 100 | 47.5 | 52.5 | 21.3 | 12.6 | 4700 |
| F9 | 100 | 52.5 | 47.5 | 18.4 | 8.4 | 4450 |

F4 to F9 were found to be unstable. That is, phase separation occurs after a week of storage at room temperature.

Example 6—Formulations Prepared with Varying Additions

Formulation F10 represents a silyl-terminated polyurea formulated as per Example 1 but without any addition of diisocyanate. Formulation F11 to F15 represent compositions with varying amounts of isophorone diisocyanate added to the reaction, such that the molar excess of primary amine to isocyanate is varied. An adhesive film was formed as in Example 2.

TABLE 2

Adhesive properties with respect to excess primary amine (* a repeat of F1)

| | Excess amine, mol % | 90° peel, N/25 mm | Loop tack, N | Viscosity at 80 °C, cP |
|---|---|---|---|---|
| F10 | — | 0.0 | 0.0 | <500 |
| F11* | 100 | 2.0 | 0.2 | 2000 |
| F12 | 33 | 2.7 | 3.0 | 9500 |
| F13 | 23 | 4.4 | 4.4 | 15000 |
| F14 | 16 | 4.9 | 11.2 | 22000 |
| F15 | 15 | 6.7 | 13.2 | 30000 |

As can be seen from the above data, the adhesive properties of the composition increase as the molar excess of primary amine decreases. Comparable adhesive properties are achieved despite the absence of a tackifier. Moreover, the compositions are stable.

TABLE 3

Adhesive properties with respect to rate of addition

| | Addition Rate | Excess amine, mol % | 90° peel, N/25 mm | Loop tack, N | Viscosity at 80° C., cP |
|---|---|---|---|---|---|
| F14 | 4 × slow constant additions over 15 minutes, spread over a total 80 minutes | 16 | 4.9 | 11.2 | 22,000 |
| F16 | Slow constant addition over 60 minutes | 16 | Cohesion failure | Cohesion failure | 54420 |
| F17 | Slow constant addition over 40 minutes | 16 | Cohesion failure | Cohesion failure | 46500 |
| F18 | Slow constant addition over 30 minutes | 16 | Cohesion failure | Cohesion failure | 45500 |
| F19 | Slow constant addition over 20 minutes | 16 | Cohesion failure | Cohesion failure | 49200 |
| F20 | Addition over 1 minute duration | 16 | 4.3 | 4.8 | 16050 |

As can be seen from the data above, the addition rate of diisocyanate into the reactor containing amines affects the resultant peel, tack and viscosity of the adhesive.

TABLE 4

Comparison with commercially available patches.

| | Type | 90° peel, N/25 mm |
|---|---|---|
| F2 | Silyl terminated polyurea with tackifiers matrix | 1.6 |
| F3 | Silyl terminated polyurea with tackifiers matrix | 3.7 |
| F13 | Silyl terminated polyurea no tackifiers matrix | 4.4 |
| F14 | Silyl terminated polyurea no tackifiers matrix | 4.9 |
| F15 | Silyl terminated polyurea no tackifiers matrix | 6.7 |
| F14 with cannabidiol patch | Silyl terminated polyurea no tackifiers matrix | 1.1 |
| F14 with varenicline patch | Silyl terminated polyurea no tackifiers matrix | 3.5 |

TABLE 4-continued

| Comparison with commercially available patches. | |
|---|---|
| Type | 90° peel, N/25 mm |
| Nurofen ™ patch | 1.0 |
| Lidocare ™ patch | 1.1 |
| Salonpas ™ patch | 1.1 |
| KefenTech ™ patch | 2.4 |
| Kinesiology ™ tape | 2.6 |
| Surgical tape | 2.5 |
| Elastoplast ™ | 3.5 |

As evidenced by the data in table 4, the compositions of the invention provide adhesion comparable to many existing transdermal drug patches without the requirement for a tackifier.

Figure 2:
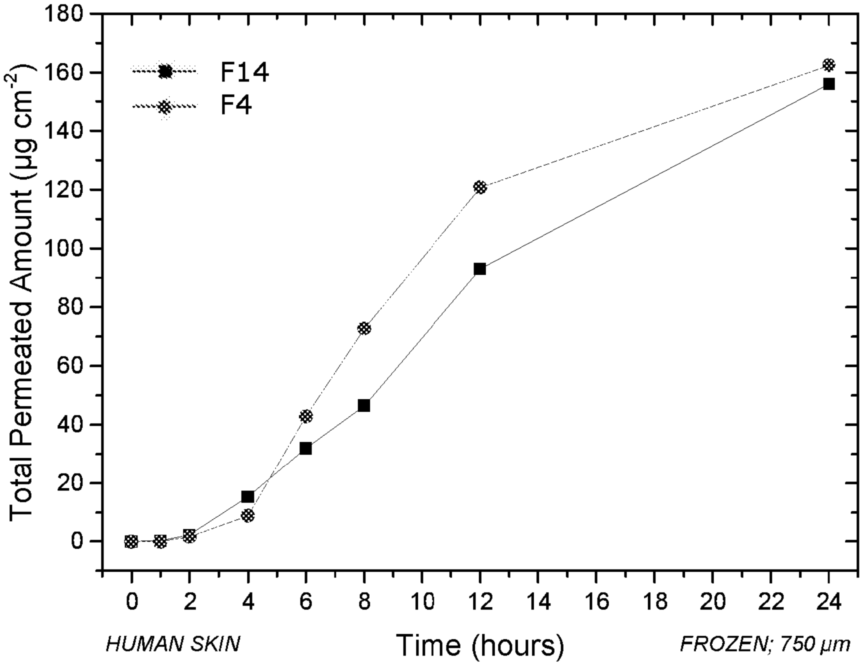
FIG. 2 shows—Permeation of varenicline through human skin from formulations F14 and F4 with varenicline.

Since one of the main applications of this novel adhesive is to be used in the manufacturing of transdermal patches, the permeation of a model drug through human skin mimicking membranes (Strat-M) was investigated. The permeation rate of a cannabidiol patch synthesized with the two different adhesive types (with and without tackifiers) was compared. As it can be seen in FIGS. 1 and 2 the exclusion of tackifiers from the adhesive formula had no effect on the permeation of the drug through human skin mimicking membranes.

Example 7—Silyl Terminated Polyurea (F14 with Cannabidiol)

5 g of cannabidiol, 2 g of titanium (IV) butoxide, 12 g of diethylene glycol monoethyl ether, 3 g of octadecanol were added to a vessel containing 78 g of silyl terminated polyurea. The mixture was homogenised at 80° C. by stirring at 120 rpm for 30 minutes. Once homogenised, the mixture was cast on PET substrate as a thin film of 130 micron by passing under a heated blade. The film was kept at a temperature of 80° C. for 5 minutes in a humid atmosphere, with greater than 50% relative humidity. The film of liquid mixture crosslinked into the form of pressure sensitive adhesive containing cannabidiol with excipients.

Example 8—Silyl Terminated Polyurea with Tackifiers (F3 with Cannabidiol)

A vessel containing 46.8 g of hydrogenated rosin ester (Arakawa KE311) tackifying resin and 31.2 g of silyl terminated polyurea was heated to 120° C. under a nitrogen atmosphere. The mixture was homogenised by stirring at 120 rpm for 3 hours. The vessel was then cooled to 80° C. 5 g of cannabidiol, 2 g of titanium (IV) butoxide, 12 g of diethylene glycol monoethyl ether, 3 g of octadecanol were added to the vessel now containing 78 g of homogenised silyl terminated polyurea and Arakawa KE311 tackifying resin. The mixture was homogenised at 80° C. by stirring at 120 rpm for 30 minutes. Once homogenised, the mixture was cast on PET substrate as a thin film of 130 micron by passing under a heated blade. The film was kept at a temperature of 80° C. for 5 minutes in a humid atmosphere, with greater than 50% relative humidity. The film of liquid mixture crosslinked into the form of pressure sensitive adhesive containing cannabidiol with excipients.

Example 9—Permeation Experiment with Synthetic Membrane 0.5 $cm^2$ sample discs were cut from the mother rolls of the above formulations and attached to Strat-M™ membranes. Obtained test specimens were placed into a diffusion cell (Franz cell) to measure the amount of cannabidiol permeated across Strat-M™ membranes over 24 hours. The acceptor solution and diffusion cells were kept at 36° C. Acceptor solution samples were regularly taken from the diffusion cell and analysed on a HPLC instrument using a validated method. See FIG. 1.

Example 10—Silyl Terminated Polyurea (F14 with Varenicline)

0.15 g of varenicline, 0.2 g of titanium (IV) butoxide, 0.3 g of propylene glycol, 0.5 g of diethylene glycol monoethyl ether, 0.5 g of dimethyl sulfoxide were added to a vessel containing 8.35 g of silyl terminated polyurea. The mixture was homogenised at 80° C. by stirring at 120 rpm for 30 minutes. Once homogenised, the mixture was cast on PET substrate as a thin film of 130 micron by passing under a heated blade. The film was kept at a temperature of 80° C. for 5 minutes in a humid atmosphere, with greater than 50% relative humidity. The film of liquid mixture crosslinked into the form of pressure sensitive adhesive containing varenicline with excipients.

Example 11—Silyl Terminated Polyurea with Tackifiers (F4 with Varenicline)

A vessel containing 4.175 g of hydrogenated rosin ester (Arakawa KE311) tackifying resin and 4.175 g of silyl terminated polyurea was heated to 120° C. under a nitrogen atmosphere. The mixture was homogenised by stirring at 120 rpm for 3 hours. The vessel was then cooled to 80° C. 0.15 g of varenicline, 0.2 g of titanium (IV) butoxide, 0.3 g of propylene glycol, 0.5 g of diethylene glycol monoethyl ether, 0.5 g of dimethyl sulfoxide were added to a vessel containing 8.35 g of silyl terminated polyurea. To the vessel now containing 8.35 g of homogenised silyl terminated polyurea, a hydrogenated rosin ester (Arakawa KE311) tackifying resin was added. The mixture was homogenised at 80° C. by stirring at 120 rpm for 30 minutes. Once homogenised, the mixture was cast on PET substrate as a thin film of 130 micron by passing under a heated blade. The film was kept at a temperature of 80° C. for 5 minutes in a humid atmosphere, with greater than 50% relative humidity. The film of liquid mixture crosslinked into the form of pressure sensitive adhesive containing varenicline with excipients.

Example 12—Permeation Experiment with Human Skin 0.5 $cm^2$ sample discs were cut from the mother rolls of the above formulations and attached to 750 μm human skin. Obtained test specimens were placed into a diffusion cell (Franz cell) to measure the amount of varenicline permeated across human skin over 24 hours. The acceptor solution and diffusion cells were kept at 36° C. Acceptor solution samples were regularly taken from the diffusion cell and analysed on a HPLC instrument using a validated method. See FIG. 2.

Example 13—S-PURE Synthesis

Additional adhesive compositions according to the invention were prepared as set out below. S-PURE is a trade name for the adhesives of the invention.

Synthesis of S-PURE D5.0

Jeffamine D-4000™ (amine content: 0.49, 4700 g, 1.18 mol, 1 eq.) was charged in a reactor vessel and heated to 85±2° C. under dry nitrogen with an initial stirring speed of 120 rpm. After the required temperature was reached, the stirring speed was increased at 180 rpm and IPDI (121.58 g, 0.55 mol, 0.47 eq.) was added using a metering pump at a flow rate of 20 ml/min ensuring the addition was between 5 and 7 min. The mixture was allowed to react such that the entire step took 15 min from the start of the IPDI addition. Then, IPTMS (235.79 g, 1.19 mol, 0.99 eq.) was added using a syringe in bulk and the reaction was allowed to proceed for 20 min from the addition of IPTMS. Finally, APTMS (10.30 g, 0.06 mol, 0.05 eq.) was added using a syringe in bulk and the reaction was also allowed to proceed for 20 min from the addition of APTMS. The final product was analysed by FT-IR to confirm the absence of residual isocyanate groups and stored under a nitrogen blanket.

Synthesis of S-PURE D5.1

Jeffamine D-4000™ (amine content: 0.49, 4700 g, 1.18 mol, 1 eq.) was charged in a reactor vessel and heated to 85±2° C. under dry nitrogen with an initial stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react for 15 min from the addition of the IPDI. IPTMS (134.45 g, 0.70 mol, 0.59 eq.) was then added using a syringe in bulk and the reaction was allowed to proceed for 20 min from the addition of IPTMS. Finally, APTMS (5.87 g, 0.03 mol, 0.03 eq.) was added using a syringe in bulk and the reaction was also allowed to proceed for 20 min from the addition of APTMS. The final product was analysed by FT-IR to confirm the absence of residual isocyanate groups and stored under a nitrogen blanket.

Synthesis of S-PURE D5.2

Jeffamine D-4000™ (amine content: 0.49, 4700 g, 1.18 mol, 1 eq.) was charged in a reactor vessel and heated to 85±2° C. under dry nitrogen with a stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react such that the entire step took 15 min from the addition of IPDI. A third addition of IPDI (27.43 g, 0.12 mol, 0.10 eq.) was followed at a flow rate of 5.2 mL/min ensuring the addition was between 4 and 6 min. The mixture was allowed to react such that the entire step took 15 min from the addition of IPDI. IPTMS (86.32 g, 0.47 mol, 0.40 eq.) was then added using a syringe in bulk and the reaction was allowed to proceed for 20 min from the addition of IPTMS. Finally, APTMS (3.77 g, 0.02 mol, 0.02 eq.) was added using a syringe in bulk and the reaction was also allowed to proceed for 20 min from the addition of APTMS. The final product was analysed by FT-IR to confirm the absence of residual isocyanate groups and stored under a nitrogen blanket.

Synthesis of S-PURE D5.3

Jeffamine D-4000™ (amine content: 0.49, 4700 g, 1.18 mol, 1 eq.) was charged in a reactor vessel and heated to 85±2° C. under dry nitrogen with a stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react such that the entire step took 15 min from the addition of IPDI. A third addition of IPDI (27.43 g, 0.12 mol, 0.10 eq.) was followed at a flow rate of 5.2 mL/min ensuring the addition was between 4 and 6 min. The mixture was allowed to react such that the entire step took 15 min from the addition of IPDI. A fourth addition of IPDI (13.03 g, 0.06 mol, 0.05 eq.) was conducted at a flow rate of 2.5 ml/min ensuring the addition was between 4 and 6 min. The mixture was allowed to react such that the entire step took 15 min from the addition of IPDI. IPTMS (63.46 g, 0.35 mol, 0.30 eq.) was then added using a syringe in bulk and the reaction was allowed to proceed for 20 min from the addition of IPTMS. Finally, APTMS (2.77 g, 0.01 mol, 0.01 eq.) was added using a syringe in bulk and the reaction was also allowed to proceed for 20 min from the addition of APTMS. The final product was analysed by FT-IR to confirm the absence of residual isocyanate groups and stored under a nitrogen blanket.

Synthesis of S-PURE D5.4

Jeffamine D-4000™ (amine content: 0.49, 4700 g, 1.18 mol, 1 eq.) was charged in a reactor vessel and heated to 85±2° C. under dry nitrogen with a stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react such that the entire step took 15 min from the addition of IPDI. A third addition of IPDI (27.43 g, 0.12 mol, 0.10 eq.) was followed at a flow rate of 5.2 mL/min ensuring the addition was between 4 and 6 min. The mixture was allowed to react such that the entire step took 15 min from the addition of IPDI. A fourth addition of IPDI (13.03 g, 0.06 mol, 0.05 eq.) was conducted at a flow rate of 2.5 ml/min ensuring the addition was between 4 and 6 min. The mixture was allowed to react such that the entire step took 15 min from the addition of IPDI. A fifth addition of IPDI (6.19 g, 0.03 mol, 0.03 eq.) was performed at a flow rate of 1.2 ml/min ensuring the addition was between 4 and 6 min. The mixture was allowed to react such that the entire step took 15 min from the addition of IPDI. IPTMS (52.60 g, 0.30 mol, 0.25 eq.) was then added using a syringe in bulk and the reaction was allowed to proceed for 20 min from the addition of IPTMS. Finally, APTMS (2.30 g, 0.01 mol, 0.01 eq.) was added using a syringe in bulk and the reaction was also allowed to proceed for 20 min from the addition of APTMS. The final product was analysed by FT-IR confirm the absence of residual isocyanate groups and stored under a nitrogen blanket.

Synthesis of S-PURE D5.5

Jeffamine D-4000™ (amine content: 0.49, 4700 g, 1.18 mol, 1 eq.) was charged in a reactor vessel and heated to 85±2° C. under dry nitrogen with a stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react such that the entire step took 15 min from the addition of IPDI. A third addition of IPDI (27.43 g, 0.12 mol, 0.10 eq.) was followed at a flow rate of 5.2 mL/min ensuring the addition was between 4 and 6 min. The mixture was allowed to react such that the entire step took 15 min from the addition of IPDI. A fourth addition of IPDI (13.03 g, 0.06 mol, 0.05 eq.) was conducted at a flow rate of 2.5 mL/min ensuring the addition was between 4 and 6 min. The mixture was allowed to react such that the entire step took 15 min from the addition of IPDI. A fifth addition of IPDI (6.19 g, 0.03 mol, 0.03 eq.) was followed at a flow rate of 1.2 mL/min ensuring the addition was between 4 and 6 min. The mixture was allowed to react such that the entire step took 15 min from the addition of IPDI. A sixth addition of IPDI (2.94 g, 0.01 mol, 0.01 eq.) occurred at a flow rate of 0.6 mL/min ensuring the addition was between 4 and 6 min. The mixture was allowed to react such that the entire step took 15 min from the addition of IPDI. IPTMS (47.44 g, 0.28 mol, 0.24 eq.) was then added using a syringe in bulk and the reaction was allowed to proceed for 20 min from the addition of IPTMS. Finally, APTMS (2.07 g, 0.01 mol, 0.01 eq.) was added using a syringe in bulk and the reaction was also allowed to proceed for 20 min from the addition of APTMS. The final product was analysed by FT-IR to confirm the absence of residual isocyanategroups and stored under a nitrogen blanket.

Synthesis of S-PURE D5.6

Jeffamine D-4000™ (amine content: 0.49, 4700 g, 1.18 mol, 1 eq.) was charged in a reactor vessel and heated to 85±2° C. under dry nitrogen with a stirring speed of 120 rpm. After the required temperature was reached, the stirring speed was increased at 180 rpm and IPDI (121.58 g, 0.55 mol, 0.47 eq.) was added using a metering pump at a flow rate of 20 mL/min ensuring the addition was between 5 and 7 min. The mixture was allowed to react such that the entire step took 15 min from the start of the IPDI addition. Then, a second addition of IPDI (57.75 g, 0.26 mol, 0.22 eq.) occurred at a flow rate of 11 ml/min ensuring the addition was between 4 and 6 min. The mixture was allowed to react such that the entire step took 15 min from the addition of IPDI. A third addition of IPDI (27.43 g, 0.12 mol, 0.10 eq.) was followed at a flow rate of 5.2 mL/min ensuring the addition was between 4 and 6 min. The mixture was allowed to react such that the entire step took 15 min from the addition of IPDI. A fourth addition of IPDI (13.03 g, 0.06 mol, 0.05 eq.) was conducted at a flow rate of 2.5 ml/min ensuring the addition was between 4 and 6 min. The mixture was allowed to react such that the entire step took 15 min from the addition of IPDI. A fifth addition of IPDI (3.09 g, 0.01 mol, 0.01 eq.) was followed at a flow rate of 0.6 mL/min ensuring the addition was between 4 and 6 min. The mixture was allowed to react such that the entire step took 15 min from the addition of IPDI. IPTMS (58.04 g, 0.33 mol, 0.28 eq.) was then added using a syringe in bulk and the reaction was allowed to proceed for 20 min from the addition of IPTMS. Finally, APTMS (2.53 g, 0.01 mol, 0.01 eq.) was added using a syringe in bulk and the reaction was also allowed to proceed for 20 min from the addition of APTMS. The final product was analysed by FT-IR to confirm the absence of residual isocyanate groups and stored under a nitrogen blanket.

Synthesis of S-PURE D6.2A—Comparative

A mixture of 90:10 molar ratio of Jeffamine D-4000™ (amine content: 0.49, 4463.1 g, 1.12 mol) and Jeffamine D-2000™ (amine content: 1.01, 240.6 g, 0.12 mol) was charged in a reactor vessel and heated to 85±2° C. under dry nitrogen with a stirring speed of 120 rpm. After the required temperature was reached, the stirring speed was increased at 180 rpm and IPDI (128.28 g, 0.72 mol, 0.58 eq. with the respect to the total moles of poly(etheramines)) was added using a metering pump at a flow rate of 20 ml/min ensuring the addition was between 5 and 7 min. The mixture was allowed to react such that the entire step took 15 min from the start of the IPDI addition. Then, a second addition of IPDI (60.93 g, 0.34 mol, 0.27 eq. with the respect to the total moles of poly(etheramines)) occurred at a flow rate of 11 ml/min ensuring the addition was between 4 and 6 min. The mixture was allowed to react such that the entire step took 15 min from the addition of IPDI. A third addition of IPDI (28.94 g, 0.16 mol, 0.13 eq. with the respect to the total moles of poly(etheramines)) was followed at a flow rate of 5.2 mL/min ensuring the addition was between 4 and 6 min. The mixture was allowed to react such that the entire step took 15 min from the addition of IPDI. A fourth addition of IPDI (13.75 g, 0.08 mol, 0.06 eq. with the respect to the total moles of poly(etheramines)) was conducted at a flow rate of 2.5 mL/min ensuring the addition was between 4 and 6 min. The mixture was allowed to react such that the entire step took 15 min from the addition of IPDI. A fifth addition of IPDI (6.53 g, 0.04 mol, 0.03 eq. with the respect to the total moles of poly(etheramines) was performed at a flow rate of 1.2 mL/min ensuring the addition was between 4 and 6 min. The mixture was allowed to react such that the entire step took 15 min from the addition of IPDI. IPTMS (55.50 g, 0.27 mol, 0.22 eq. with the respect to the total moles of poly(etheramines)) was then added using a syringe in bulk and the reaction was allowed to proceed for 20 min from the addition of IPTMS. Finally, APTMS (2.42 g, 0.01 mol, 0.01 eq. with the respect to the total moles of poly(etheramines)) was added using a syringe in bulk and the reaction was also allowed to proceed for 20 min from the addition of APTMS. The final product was analysed by FT-IR to confirm the absence of residual isocyanate groups and stored under a nitrogen blanket.

The different compositions and ratios of D4000:IPDI are summarised below.

TABLE 5 conditions for preparing S-PURE adhesive compositions.

| S-PURE Variant | D4000:IPDI content (mol ratio) | Number of IPDI Additions |
|---|---|---|
| S-PURE-D5.0 | 1:0.47 | 1 |
| S-PURE-D5.1 | 1:0.69 | 2 |
| S-PURE-D5.2 | 1:0.79 | 3 |
| S-PURE-D5.3 | 1:0.84 | 4 |
| S-PURE-D5.4 | 1:0.87 | 5 |
| S-PURE-D5.5 | 1:0.88 | 6 |
| S-PURE-D5.6 | 1:0.85 | 5 |

Example 14—Preparation of Adhesive Patches

Titanium (IV) butoxide catalyst (1%) was added to a representative amount of the S-PURE compositions described above and the resultant mix was spread using an RK K-Control coater set at 80° C. using a K-Bar. The resultant patch was subjected to 1.5 minutes of steam and a further 3.5 minutes of heat to induce curing of the prepolymer. Curing was assessed after 5 min total time.

Example 15—Amplitude Sweep Experiments

Figure 3:
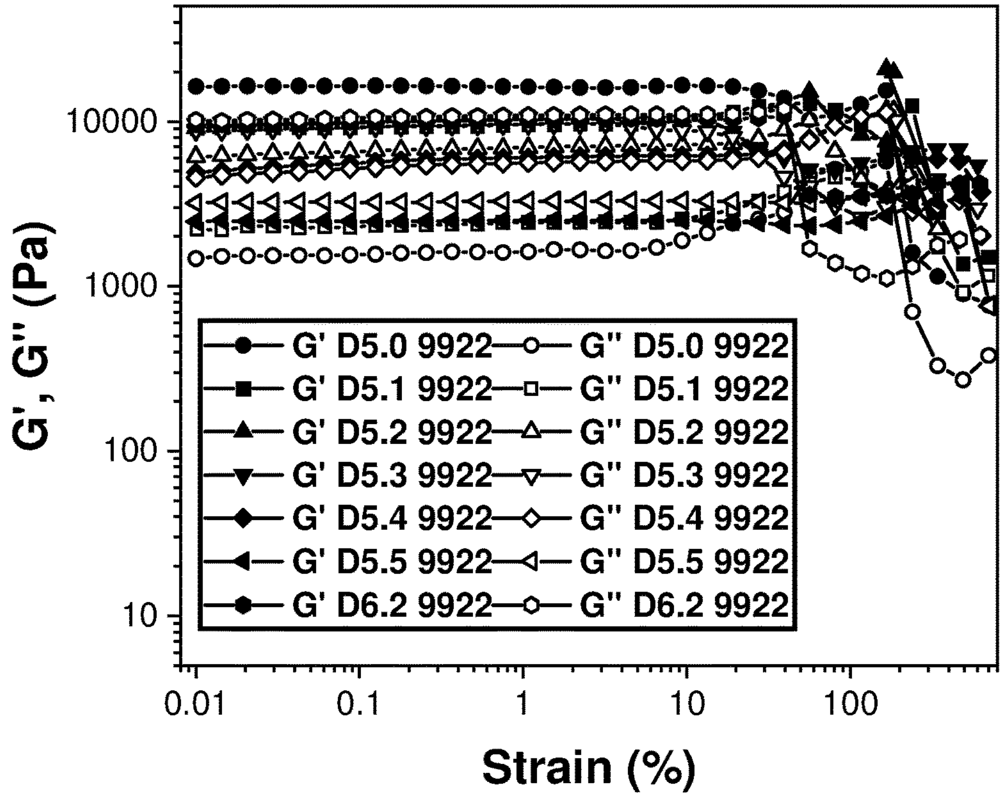
FIG. 3 shows—the % strain where the storage modulus G' plateaus for a number of different compositions according to the invention.

The table below shows the strain (%) range where the storage modulus (G') plateaus. At high strains (%) (>30%), sample slippage was observed, and viscoelastic characteristics could not be measured further. The results are shown in FIG. 3 and in Table 6 below:

TABLE 6

LVER regions based on amplitude sweep experiments.

| Entry | LVER-Strain (%) Range |
|---|---|
| S-PURE-D5.0 | 0.01-28 |
| S-PURE-D5.1 | 0.01-20 |
| S-PURE-D5.2 | 0.01-28 |
| S-PURE-D5.3 | 0.01-13 |
| S-PURE-D5.4 | 0.01-28 |
| S-PURE-D5.5 | — |
| S-PURE-D6.2 | 0.01-39 |

Figure 4:
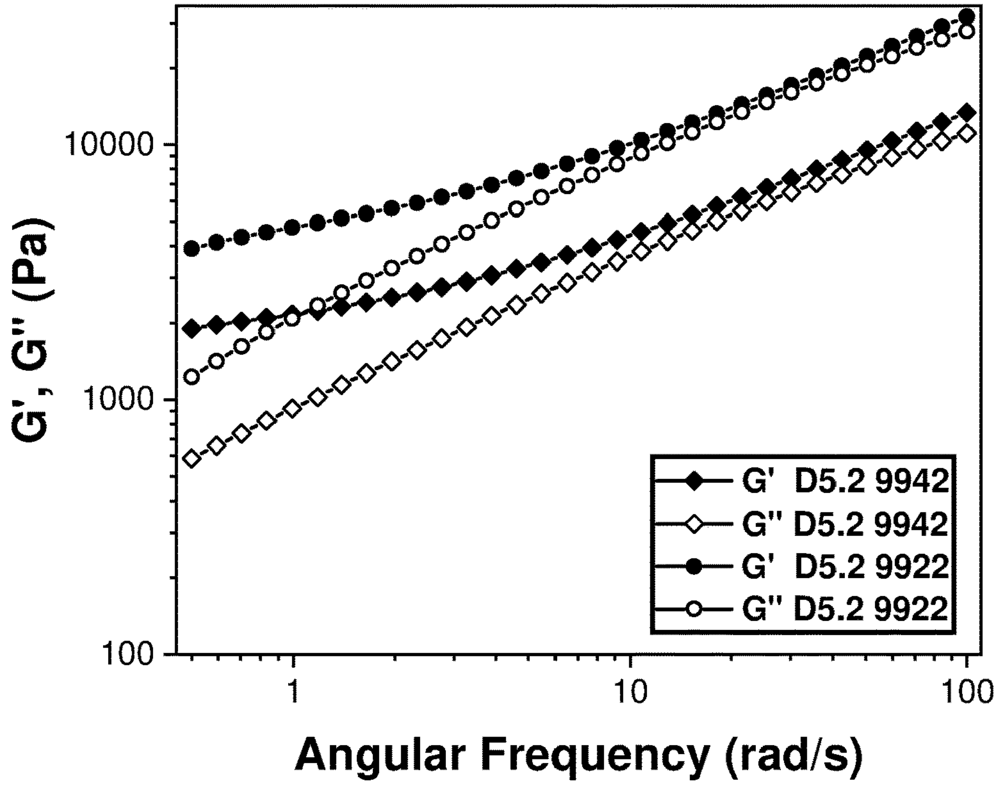
FIG. 4 shows—the G', G" at different angular frequency for an example composition (D5.2) at 9922 (130 μm) and 9942 (50 μm) thickness.
Figure 5:
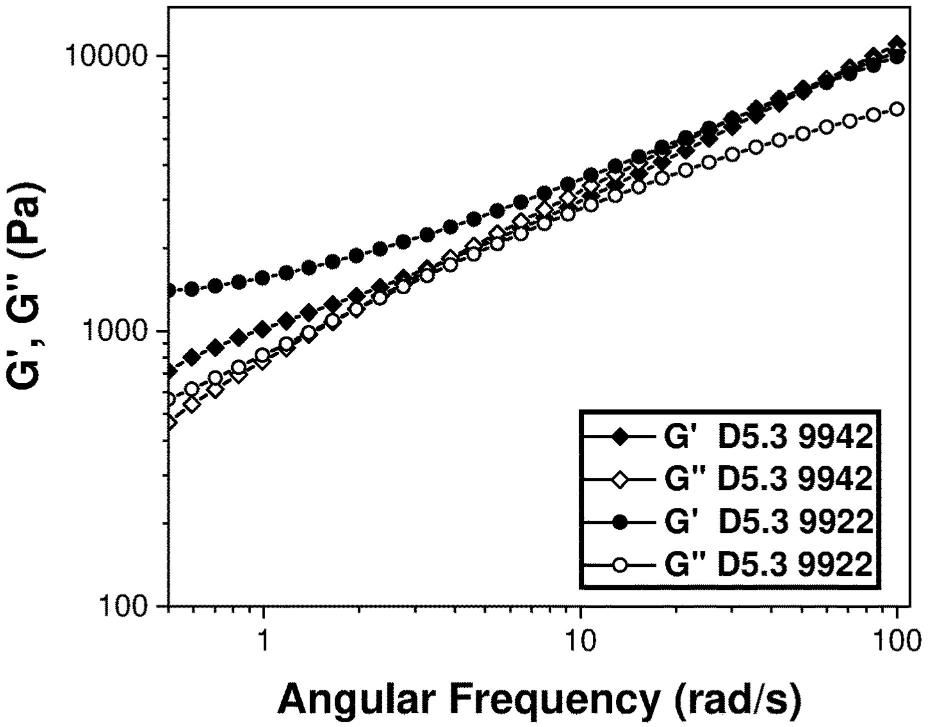
FIG. 5 shows—the G', G" at different angular frequency for an example composition (D5.3) at 9942 (50 μm) and 9922 (130 μm) thickness.

The effect of patch thickness was studied where 9922 (130 μm)>9942 (50 μm). Frequency sweep experiments were performed at a constant strain (%) of $\gamma$=1.0% (as dictated by the previously found LVER regions). As expected, the results showed that an increase in the thickness led to larger G' values indicative of stiffer and more elastic materials. Despite the difference in thickness, samples demonstrated similar viscoelastic profiles up to $\omega$=100 rad/s where the value of G' almost equalled the value of G". A continues increase in the G' values was noticed by increasing the frequency of deformation attributed to the existence of polymer entanglements. The results for the S-PURE D5.2 and D5.3 formulations are shown in FIGS. 4 and 5 respectively.

Figure 6:
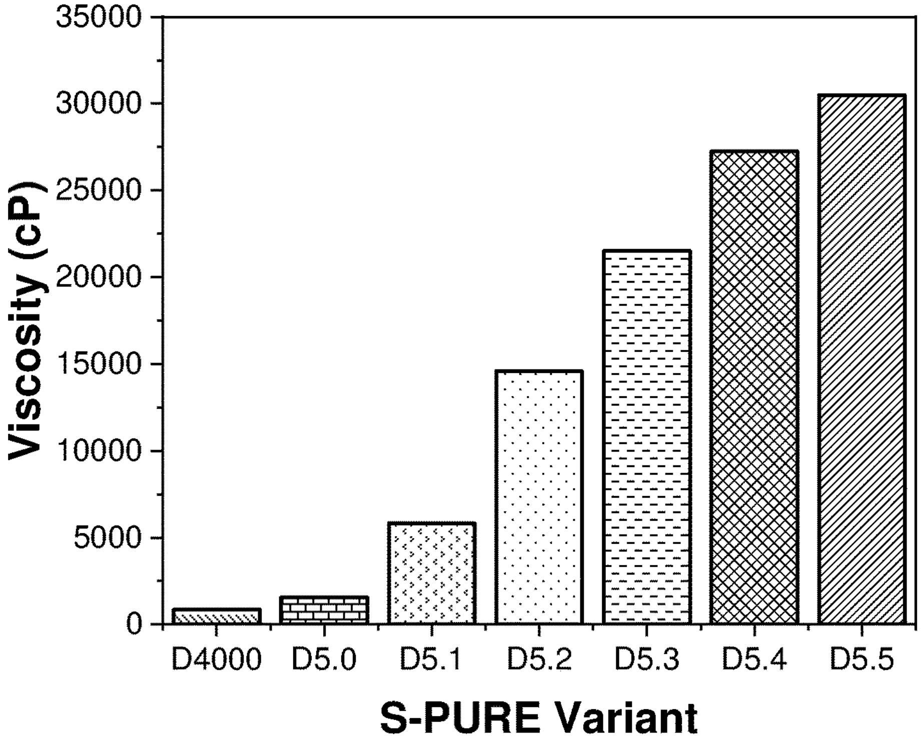
FIG. 6 shows—the viscosity for different polymer compositions.

The effect of different average molecular weights between crosslinks (Mc) was investigated by analysing formulations made from polymers with various molecular weights. Initially viscometry was used to assess the difference in molecular weight. Polymers formed from higher IPDI to Jeffamine® D4000 ratios had longer polymer chains during the step-growth polymerization process, which leads to higher average molecular weights and thus higher viscosities. The results are shown in FIG. 6.

Figure 7:
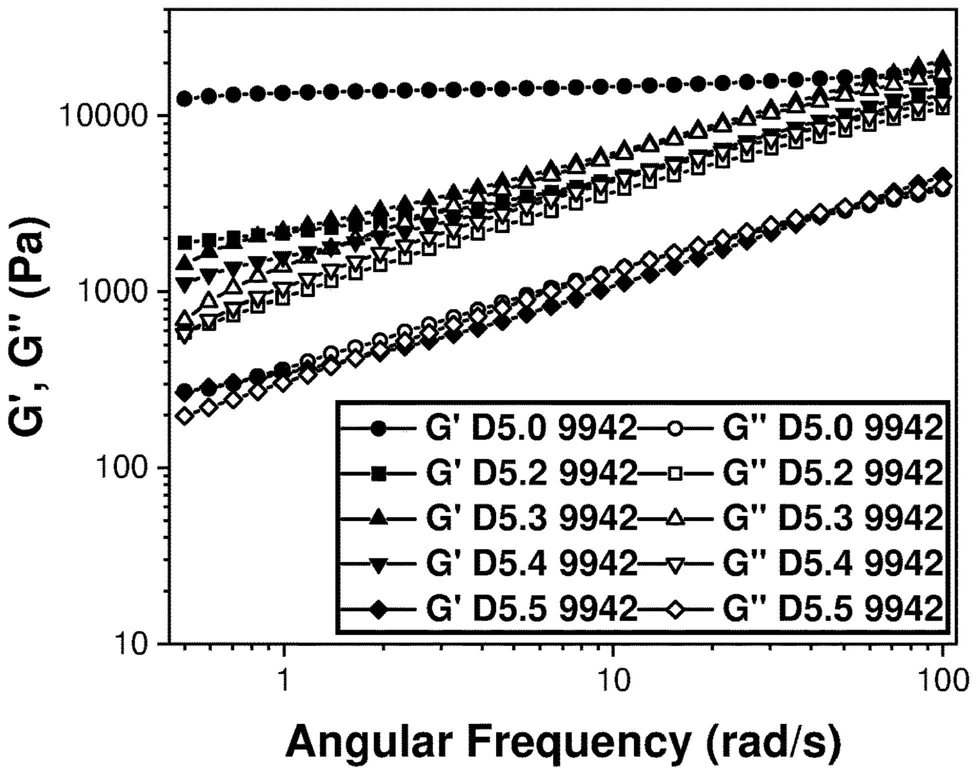
FIG. 7 shows—frequency sweep experiments on different polymers at a thickness of 9942 (50 μm) with a constant strain (%) of $\gamma$=1.0% at 25° C.
Figure 8:
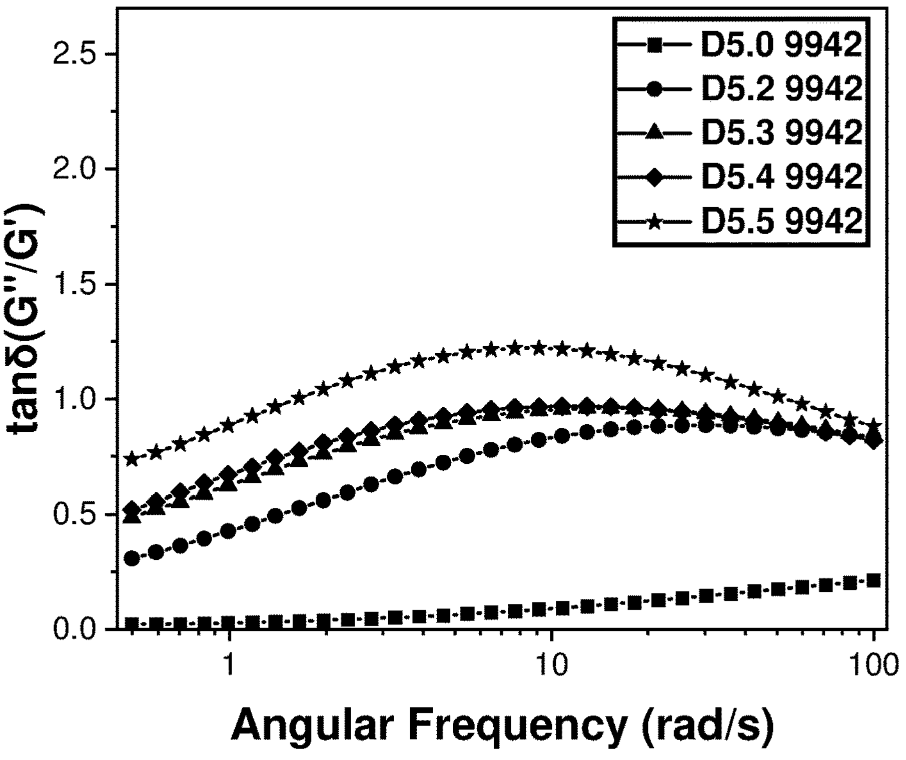
FIG. 8 shows—the tan δ change during frequency sweep experiments.

Frequency sweep experiments were performed on different S-PURE variants at a thickness of 9942 (50 μm). The results in FIG. 7 show that higher molecular weight S-PURE variants had lower G' values indicative of softer, more wettable and thus more adhesive surfaces. Generally, the average molecular weight of the polymers is expected to be analogous to the average molecular weight between crosslinks (Mc) the increase of which leads to lower crosslink densities. D5.0 demonstrated a constant rheological profile with the G' values plateauing by increasing angular frequency in contrast to the rest of the formulations where the G' kept increasing by the frequency of deformation a result of polymer entanglements and higher average molecular weight. In addition, D5.5, which had the highest molecular weight, demonstrated the lowest G' and G" values which cross over at a frequency of ~1.1 turning the adhesive into a viscous fluid with the G" exceeding the G' throughout. This was also showcased by the values of tan $\delta$ which were >1 for D5.5 and lower <1 for the lower molecular weight S-PURE variants which showed a more viscoelastic type of character (FIG. 8).

Figure 9:
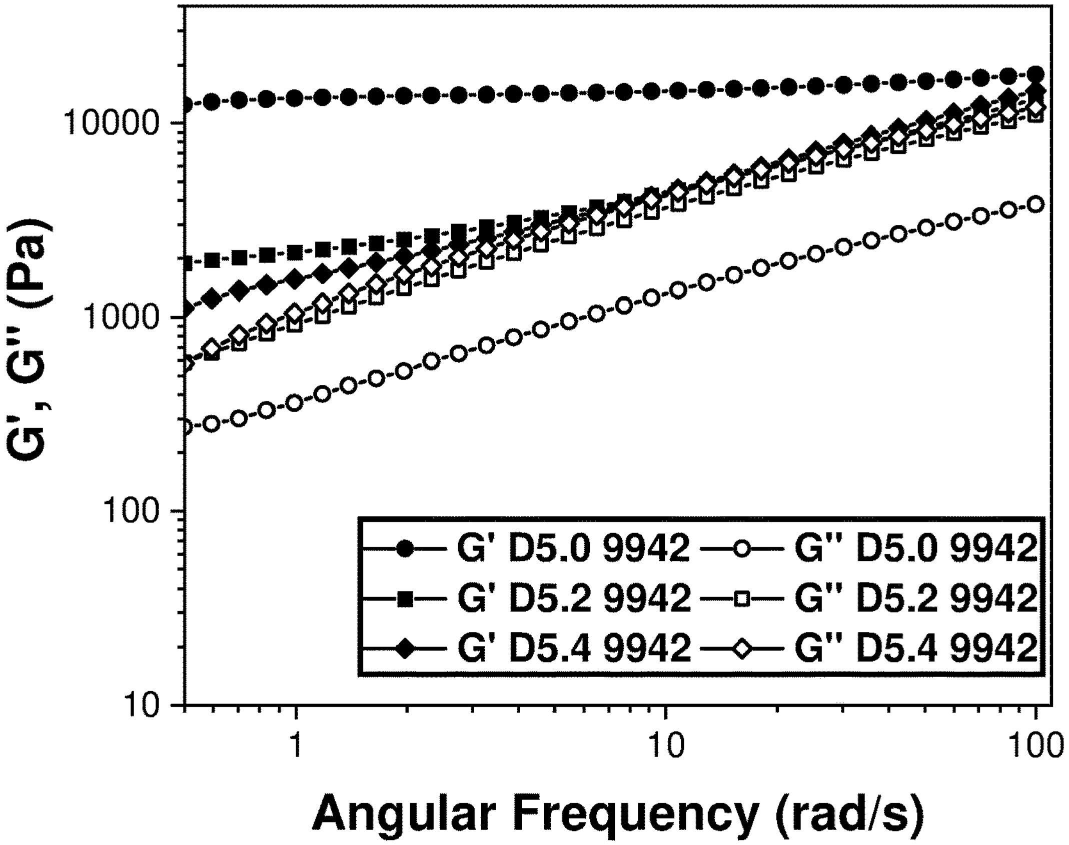
FIG. 9 shows—frequency sweep comparison between D5.0, D5.2 and D5.4 compositions highlighting the different G' and G" trends at high angular frequencies. Experiments conducted at a constant strain (%) of $\gamma$=1.0% at 25° C.
Figure 10:
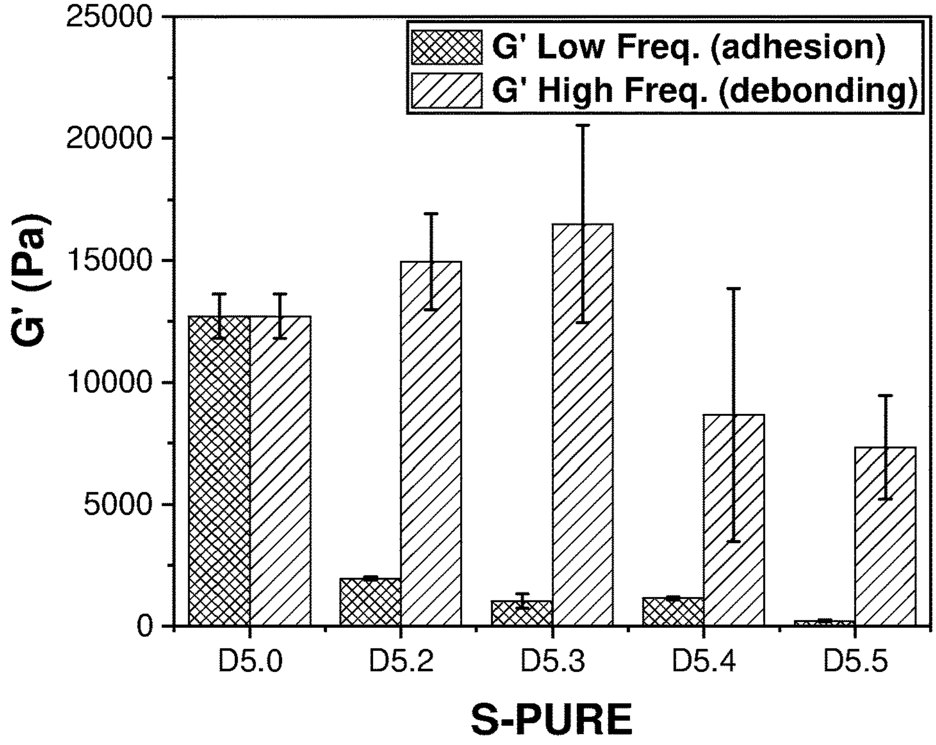
FIG. 10 shows—G' values at low and high angular frequencies for different compositions. The G' at low frequencies represents adhesion and at high frequency represents the debonding process.

The different trends of G' and G" at high angular frequencies are shown in FIG. 9 where the increase in molecular weight brought the two values closer to each other in a "parallel" way though without crossing over to turn into a fluid like state. An overall chart of the G' values at low (indicative of adhesion) and high (indicative of peeling) angular frequencies is illustrated in FIG. 10.

Figure 11:
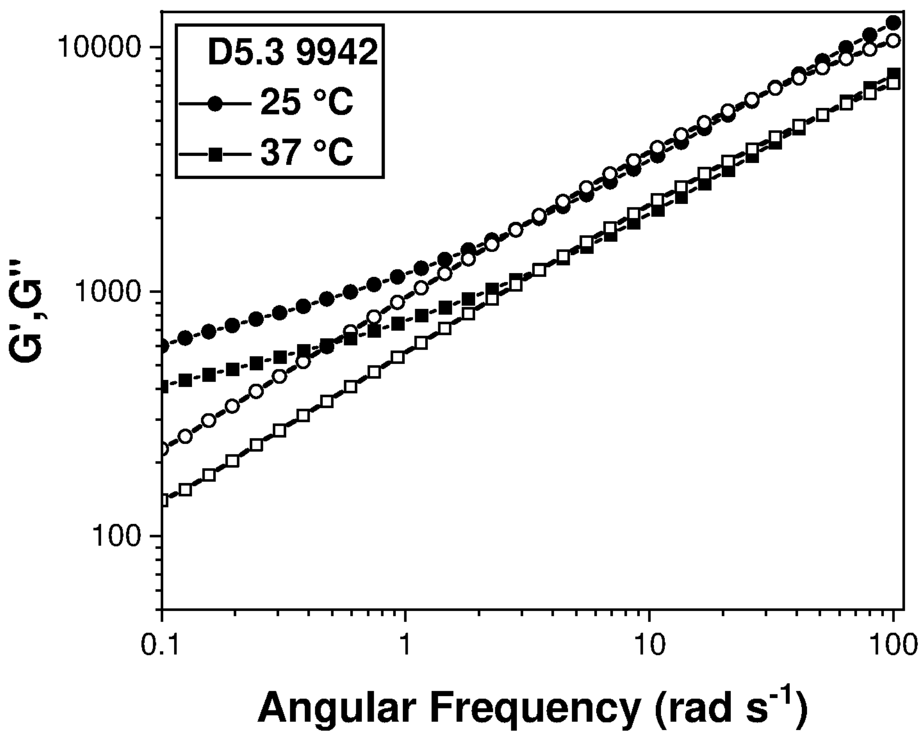
FIG. 11 shows—The effect of temperature by frequency sweep experiments.
Figure 12:
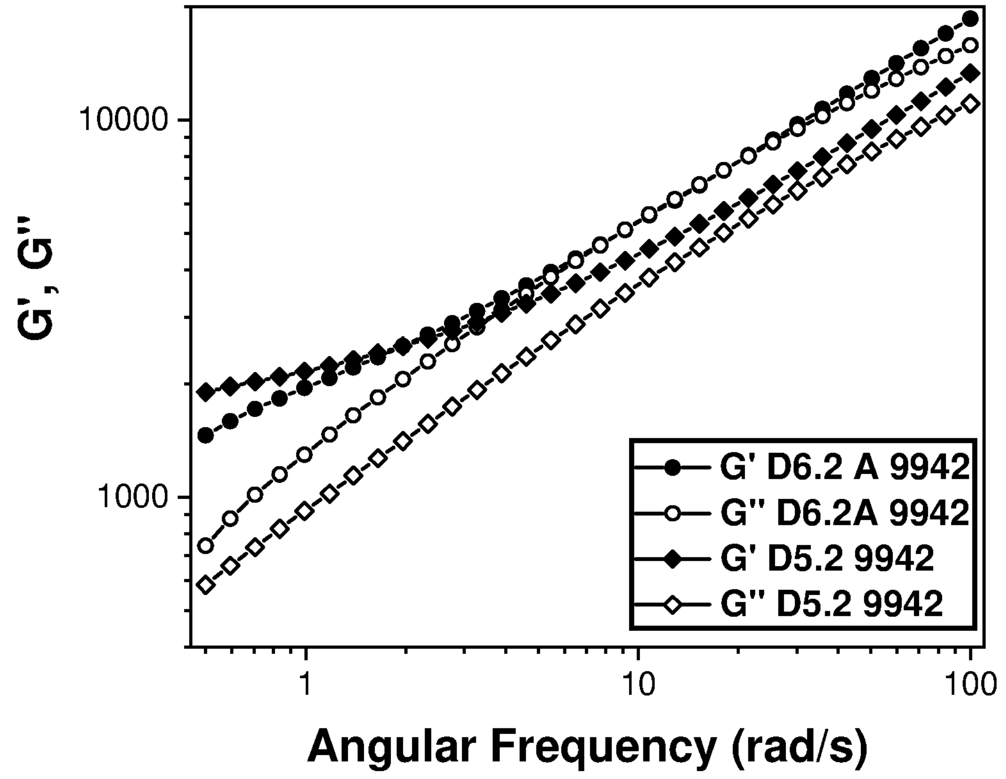
FIG. 12 shows—Rheological comparison of compositions made from a different molecular weight starting materials.

The effect of temperature was also investigated on D5.3 9942 samples by comparing their viscoelastic behaviour at 25 and 37° C. The results are shown in FIG. 11. An increase in temperature can affect the viscoelastic characteristics by lowering both the G' and G" values. Despite the temperature raise, the viscoelastic profiles remained the same with the G' approaching the G" at high angular frequencies without crossing indicative that the covalent crosslinked network doesn't break at the examined frequencies. The drop in G' by increasing temperature was attributed to a larger free volume of the polymer chains which makes them more mobile along with the thermal rupture of hydrogen bonds.

Finally, S-PURE formulations containing a mixture of Jeffamine D-4000™ and Jeffamine D-2000™ (D6.2A) were compared with those containing Jeffamine® D4000 (D5.2) at the same thickness (9942), Frequency sweep results indicated that D6.2A had a lower G' value than D5.2 at low angular frequencies showing that D6.2A had a better adhesion as a result of the higher amount of urea moieties per chain. At high angular frequencies the G' values of D6.2A were higher indicative of a higher peel strength than D5.2.

The tabulated results are shown in Tables 7 and 8 below.

TABLE 7

| Entry | $G'_{plateau}$ (Pa) | $G'_{0.5\ rad/s}$ (Pa) | $G'_{1\ rad/s}$ (Pa) | $G'_{100\ rad/s}$ (Pa) | G' = G" (rad/s) |
|---|---|---|---|---|---|
| SPURE D6.2A 9942 | No plateau | 1,551 ± 171 | 2,051 ± 215 | 20,811 ± 3253 | 4.9 ± 1.6 |
| SPURE D6.2A 9922 | No plateau | 1,864 ± 500 | 2,406 ± 602 | 31,461 ± 8144 | 1.7 ± 0.3 |
| SPURE D5.0 9942 | 12,711 ± 910 | Plateau | Plateau | Plateau | No crossing |
| SPURE D5.1 9942 | No plateau | 15,293 ± 6019 | 16,877 ± 6614 | 40,950 ± 16,851 | No crossing |
| SPURE D5.2 9942 | No plateau | 1,945 ± 66 | 2,321 ± 199 | 14,950 ± 1974 | Parallel |
| SPURE D5.2 9922 | No plateau | 2,891 ± 887 | 3,501 ± 1074 | 22,296 ± 8,321 | Parallel |
| SPURE D5.3 9942 | No plateau | 1,027 ± 293 | 1599 ± 488 | 16,501 ± 4053 | Parallel |
| SPURE D5.3 9922 | No plateau | 2,441 ± 981 | 3,284 ± 1209 | 24,720 ± 13,021 | Parallel |
| SPURE D5.4 9922 | No plateau | 1,650 ± 796 | 2,132 ± 1025 | 26,501 ± 13,800 | 2.0 ± 0.2 |
| SPURE D5.4 9942 | No plateau | 1,143 ± 67 | 1,620 ± 138 | 8,664 ± 5,181 | Parallel |

TABLE 7-continued

| Entry | $G'_{plateau}$ (Pa) | $G'_{0.5\ rad/s}$ (Pa) | $G'_{1\ rad/s}$ (Pa) | $G'_{100\ rad/s}$ (Pa) | G' = G" (rad/s) |
|---|---|---|---|---|---|
| SPURE D5.5-9942 | No plateau | 235 ± 25 | 316 ± 23 | 4,750 ± 373 | 1.1 ± 0.3 |
| SPURE D5.5-9922 | No plateau | 239 ± 89 | 352 ± 125 | 6,370 ± 1,705 | 0.7 ± 0.1 |

TABLE

| Entry | G' (0.01 rad/s) (Pa) | G" (0.01 rad/s) (Pa) | G' (0.5 rad/s) (Pa) | G" (0.5 rad/s) (Pa) | G' (100 rad/s) (Pa) | G" (100 rad/s) (Pa) |
|---|---|---|---|---|---|---|
| SPURE D6.2A | 309 ± 11 | 30 ± 8 | 1,551 ± 171 | 836 ± 120 | 20,811 ± 3253 | 18,334 ± 3,468 |
| SPURE D5.0 | 7,932 ± 664 | 1150 ± 462 | 12,711 ± 910 | 401 ± 273 | 12,711 ± 910 | 3,259 ± 400 |
| SPURE D5.1 | 2,255 ± 147 | 161 ± 93 | 15,293 ± 6,019 | 1,266 ± 380 | 40,950 ± 16,851 | 22,751 ± 8,215 |
| SPURE D5.2 | 563 ± 18 | 29 ± 2 | 1,945 ± 66 | 603 ± 36 | 14,950 ± 1,974 | 12,646 ± 1,572 |
| SPURE D5.3 | 315 ± 30 | 36 ± 7 | 1,027 ± 293 | 558 ± 97 | 16,501 ± 4053 | 14,420 ± 2,963 |
| SPURE D5.4 | 275 ± 47 | 17 ± 3 | 1,143 ± 67 | 597 ± 21 | 8,664 ± 5,181 | 11,673 ± 428 |
| SPURE D5.5 | 197 ± 50 | 74 ± 16 | 235 ± 25 | 187 ± 21 | 7,334 ± 2,107 | 4,657 ± 974 |

Figure 13A:
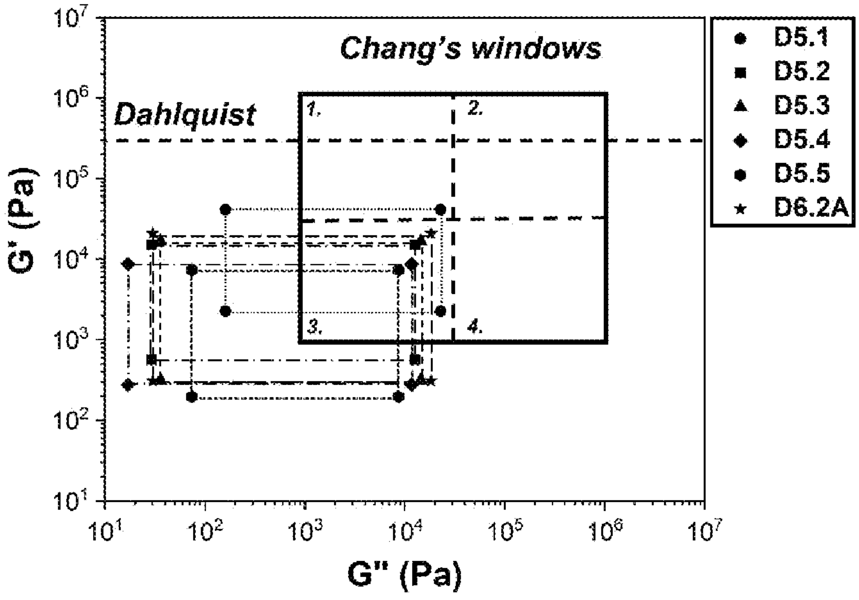
FIGS. 13(*a*) and (*b*) show-A comparison of the viscoelastic windows of different compositions at 25° C. and at a frequency of 0.01 rad/s (a) and 0.05 rad/s (b) to the Chang's viscoelastic window for adhesives shown as black lines. The dashed line corresponds to the Dahlquist criterion.
Figure 13B:
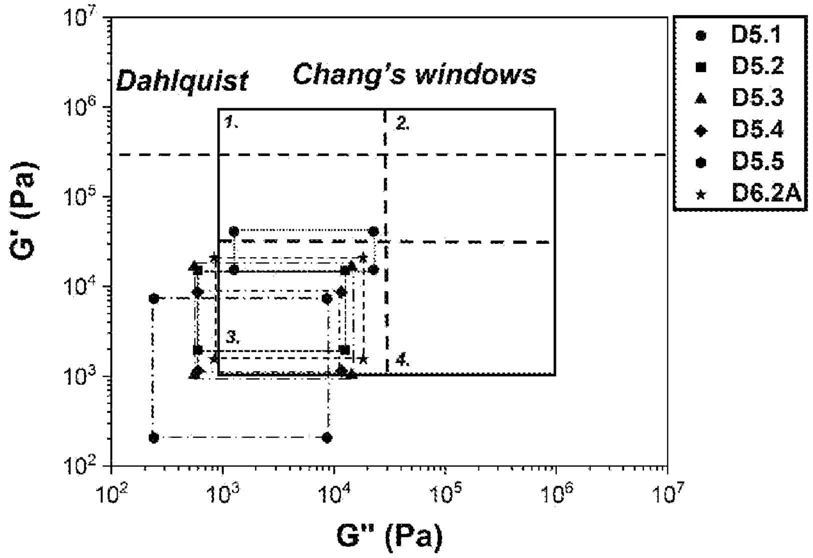

Based on the G' and G" values, viscoelastic windows were attained at 0.01 and 0.05 rad/s (FIGS. 13(*a*) and (*b*)). For the viscoelastic windows the following coordinates were used: G', G"=> (100, 0.5), (100, 100), (0.5, 0.5) and (0.5, 100) or (100, 0.01), (100, 100), (0.01, 0.01) and (0.01, 100). To assess the type of adhesive, the viscoelastic windows were compared against Chang's viscoelastic windows and the Dahlquist criterion for a good adhesive. A frequency of 0.5 rad/s is equivalent to the deformation that an adhesive experiences on skin.

According to FIGS. 13(*a*) and (*b*), all S-PURE variants fulfilled the Dahlquist criterion for a good PSA with a good contact efficiency. Surprisingly, increasing molecular weight (5.0=>5.5), the viscoelastic windows shifted to the lower left quadrant 3 characteristic of removable PSAs for medical applications characterized by a low G' with most of them exceeding the limits of the Chang's windows.

Figure 14:
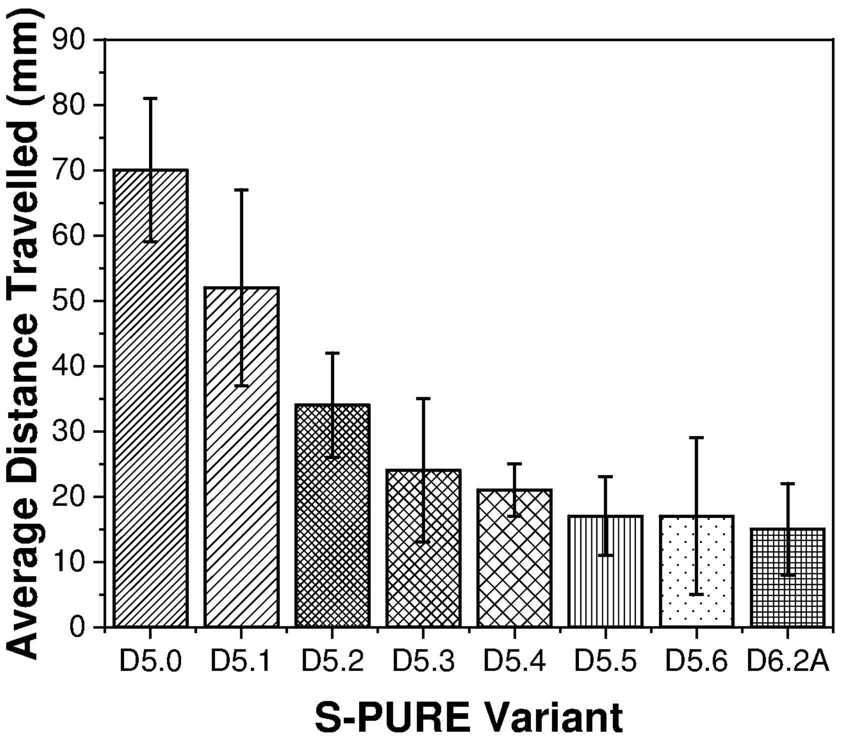
FIG. 14 shows—the results of a rolling ball tack test for various S-PURE variants.
Figure 15:
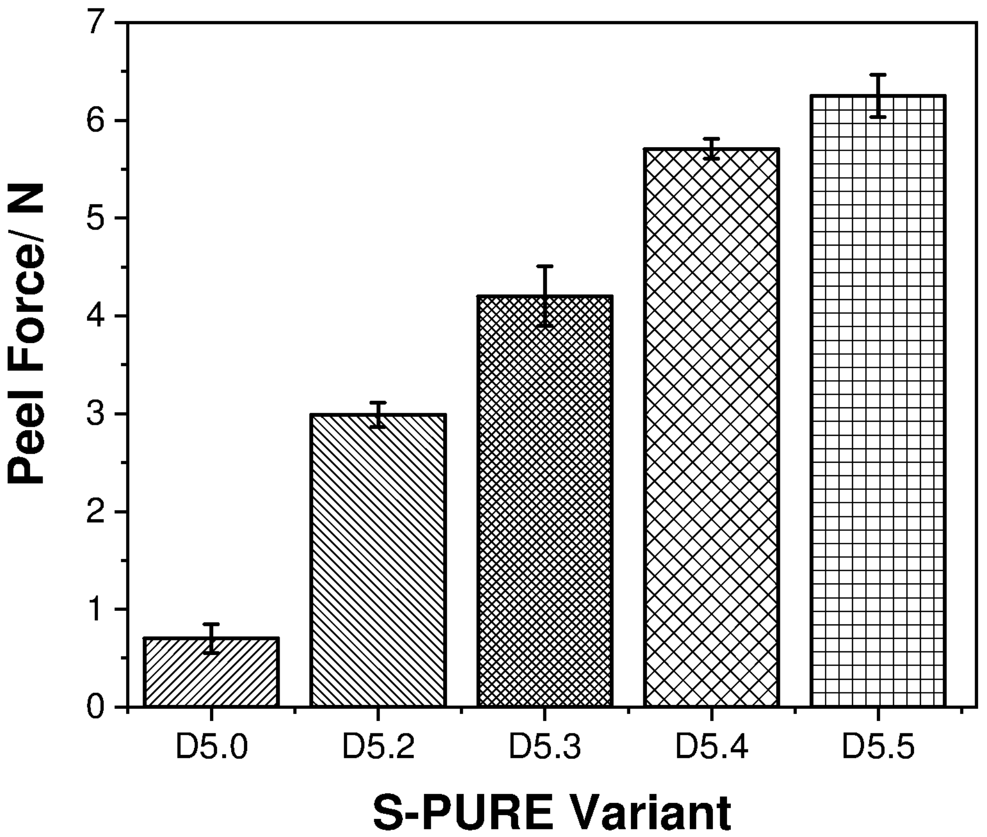
FIG. 15 shows—the results of a 90° peel back test for various compositions of the invention.

The adhesion and rolling ball tack test for the S-PURE compositions was measured and is shown below in table 9 and in FIGS. 14 and 15:

TABLE 9

| S-PURE Variant | 90° Peel Adhesion Test (N) | Rolling Ball Tack Test (mm) |
|---|---|---|
| S-PURE-D5.0 | 0.70 ± 0.15 | 70 ± 11 |
| S-PURE-D5.1 | 1.46 ± 0.13 | 52 ± 15 |
| S-PURE-D5.2 | 2.99 ± 0.13 | 34 ± 8 |
| S-PURE-D5.3 | 4.20 ± 0.31 | 24 ± 11 |
| S-PURE-D5.4 | 5.71 ± 0.10 | 21 ± 4 |
| S-PURE-D5.5 | 6.25 ± 0.22 | 17 ± 6 |
| S-PURE-D5.6 | 5.19 ± 0.30 | 17 ± 12 |

The force required to peel a patch from a stainless-steel surface increased by raising the amount of IPDI added (D5.0 to D5.5). Results indicated that 90° peel adhesion testing can be used as a method to differentiate different S-PURE formulations. The average distance travelled by the ball after it exits the ramp decreased as tackiness increased. The higher the amount of IPDI added, the greater the tackiness of S-PURE as the lower was the travelling distance of the ball. However, the differences in tackiness between the variants of S-PURE were not large enough to be able to use this parameter to distinguish between S-PURE variants.

The invention claimed is:

1. An adhesive composition comprising a crosslinked silyl-containing telechelic polyurea polymer, wherein G' and G" are less than 1000 Pa at a frequency of 0.1 rad/s at 25° C., and wherein the composition does not comprise a tackifier.

2. The adhesive composition of claim 1, wherein the adhesive composition has a G' and G" of less than 50,000 Pa at a frequency of 100 rad/s at 25° C.

3. The adhesive composition of claim 1, wherein the adhesive composition has a tan delta between 0.90 and 1.10 at at least one frequency between 0.01 and 100 rad/s at 25° C., and wherein the tan delta is not above 1.10 for any frequency between 0.01 rad/s and 100 rad/s.

4. The adhesive composition of claim 1, wherein the telechelic polyurea comprises a structure according to formula (IV):

(IV)

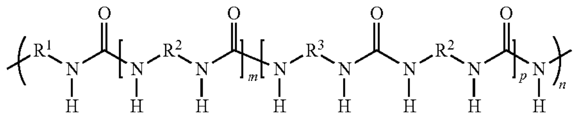

wherein

R1 is a polyether;

R2 and R3 are each independently a spacer;

n is an integer in the range of 1 to 100;

m is an integer in the range 0 to 1;

p is an integer in the range 0 to 10; and wherein the sum of m and p is >0.

5. The adhesive composition of claim 4, wherein the polyether possesses a weight average molecular weight in the range 2000 Da to 10,000 Da.

6. The adhesive composition of claim 4, wherein the polyurea has a structure according to formulae (VII) or (VIII):

(VII)

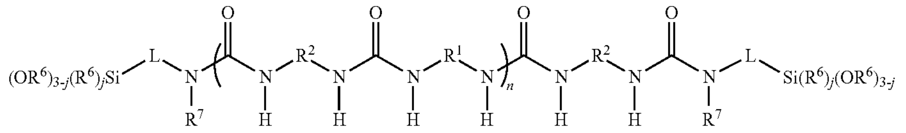

(VIII)

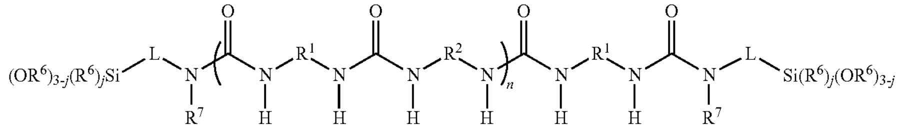

$R^1$ is a polyether;

$R^2$ is a spacer;

L is a linker selected from: alkyl, alkenyl, alkynyl, aryl, heteroaryl each of which may be optionally substituted;

$R^6$ is selected from: alkyl, alkenyl, alkynyl, aryl, heteroaryl each of which may be optionally substituted;

$R^7$ is selected from: hydrogen, optionally substituted alkyl, optionally substituted alkenyl, optionally substituted alkynyl, optionally substituted aryl or optionally substituted heteroaryl;

n is an integer in the range of 1 to 100; and j is an integer in the range of 0 to 2.

7. The adhesive composition of claim 4, wherein the spacer is selected from: optionally substituted alkyl, optionally substituted alkoxyl, optionally substituted alkenyl, optionally substituted alkynyl, optionally substituted aryl or optionally substituted heteroaryl.

8. The adhesive composition of claim 1, wherein the adhesive composition is a pressure sensitive adhesive.

* * * * *